United States Patent
Shih et al.

(10) Patent No.: US 10,286,146 B2
(45) Date of Patent: May 14, 2019

(54) IMPLANTABLE DRUG PUMPS AND REFILL DEVICES THEREFOR

(71) Applicant: MiniPumps, LLC, Pasadena, CA (US)

(72) Inventors: Jason Shih, Yorba Linda, CA (US); Sean Caffey, Hawthorne, CA (US)

(73) Assignee: MINIPUMPS, LLC, Pasadena, CA (US)

( * ) Notice: Subject to any disclaimer, the term of this patent is extended or adjusted under 35 U.S.C. 154(b) by 300 days.

(21) Appl. No.: 13/632,722

(22) Filed: Oct. 1, 2012

(65) Prior Publication Data

US 2013/0116666 A1 May 9, 2013

Related U.S. Application Data

(63) Continuation-in-part of application No. 13/419,968, filed on Mar. 14, 2012, now abandoned.
(Continued)

(51) Int. Cl.
*A61M 5/162* (2006.01)
*A61M 5/142* (2006.01)
*A61M 39/02* (2006.01)

(52) U.S. Cl.
CPC ........ *A61M 5/162* (2013.01); *A61M 5/14276* (2013.01); *A61M 39/0208* (2013.01);
(Continued)

(58) Field of Classification Search
CPC .... A61M 5/14276; A61M 2005/14204; A61M 2005/14208; A61M 2005/14284;
(Continued)

(56) References Cited

U.S. PATENT DOCUMENTS 3,731,681 A 5/1973 Blackshear et al.
3,916,899 A 11/1975 Theeuwes et al.
(Continued)

FOREIGN PATENT DOCUMENTS

CA 946696 A1 5/1974
CH 570169 A5 12/1975
(Continued)

OTHER PUBLICATIONS

"Krupin Eye Valve with Scleral Buckle, Krupin Eye Valve With Disk", Hood Laboratories Catalogue, F 079 Rev., Nov. 1992, 4 pages.
(Continued)

*Primary Examiner* — Nathan R Price
*Assistant Examiner* — Justin L Zamory
(74) *Attorney, Agent, or Firm* — Morgan, Lewis & Bockius LLP

(57) ABSTRACT

A system for refilling the drug reservoir of an implanted drug pump device may facilitate wireless data exchange between the refill system and the implanted device, e.g., to verify proper drug selection prior to commencement of the refill process. Via the wireless link, the drug pump device and refill system can exchange data such as, for example, refill information (including, e.g., a type of drug), a drug pump device history, a drug dosage log, and/or a drug-delivery protocol. Further, the refill system can facilitate reprogramming the implanted device wirelessly.

27 Claims, 12 Drawing Sheets

Related U.S. Application Data

(60) Provisional application No. 61/541,723, filed on Sep. 30, 2011, provisional application No. 61/452,399, filed on Mar. 14, 2011.

(52) U.S. Cl.
CPC ............ A61M 2205/3507 (2013.01); A61M 2205/3523 (2013.01)

(58) Field of Classification Search
CPC ......... A61M 2005/14513; A61M 2205/6009; A61M 2205/3523; A61J 2205/10; A61J 2205/40; A61J 2205/60; A61N 1/37247
USPC ................. 604/141, 288.01, 288.02, 891.1
See application file for complete search history.

(56) References Cited

U.S. PATENT DOCUMENTS

| | | |
|---|---|---|
| 3,977,404 A | 8/1976 | Theeuwes |
| 4,150,673 A | 4/1979 | Watt |
| 4,164,560 A | 8/1979 | Folkman et al. |
| 4,543,088 A | 9/1985 | Bootman et al. |
| 4,553,973 A | 11/1985 | Edgren |
| 4,573,994 A | 3/1986 | Fischell et al. |
| 4,673,394 A | 6/1987 | Fenton, Jr. et al. |
| 4,738,657 A | 4/1988 | Hancock et al. |
| 4,751,926 A | 6/1988 | Sasaki |
| 4,760,837 A | 8/1988 | Petit |
| 4,781,675 A | 11/1988 | White |
| 4,781,695 A | 11/1988 | Dalton |
| 4,804,054 A | 2/1989 | Howson et al. |
| 4,838,887 A | 6/1989 | Idriss |
| 4,853,224 A | 8/1989 | Wong |
| 4,888,176 A | 12/1989 | Langer et al. |
| 4,955,861 A | 9/1990 | Enegren et al. |
| 4,959,217 A | 9/1990 | Sanders et al. |
| 5,007,647 A | 4/1991 | Gulick |
| 5,135,499 A | 8/1992 | Tafani et al. |
| 5,147,647 A | 9/1992 | Darougar |
| 5,164,188 A | 11/1992 | Wong |
| 5,171,213 A | 12/1992 | Price, Jr. |
| 5,178,604 A | 1/1993 | Baerveldt et al. |
| 5,201,715 A | 4/1993 | Masters |
| 5,252,192 A | 10/1993 | Ludwig |
| 5,312,357 A | 5/1994 | Buijs et al. |
| 5,389,077 A | 2/1995 | Melinyshyn et al. |
| 5,407,441 A | 4/1995 | Greenbaum |
| 5,443,505 A | 8/1995 | Wong et al. |
| 5,462,739 A | 10/1995 | Dan et al. |
| 5,472,436 A | 12/1995 | Fremstad |
| 5,476,445 A | 12/1995 | Baerveldt et al. |
| 5,478,328 A | 12/1995 | Silverman et al. |
| 5,704,520 A | 1/1998 | Gross |
| 5,725,017 A | 3/1998 | Elsberry et al. |
| 5,725,493 A | 3/1998 | Avery et al. |
| 5,798,115 A | 8/1998 | Santerre et al. |
| 5,824,072 A | 10/1998 | Wong |
| 5,830,173 A | 11/1998 | Avery et al. |
| 5,836,935 A | 11/1998 | Ashton et al. |
| 5,868,697 A | 2/1999 | Richter et al. |
| 5,904,144 A | 5/1999 | Hammang et al. |
| 5,989,579 A | 11/1999 | Darougar et al. |
| 6,144,106 A | 11/2000 | Bearinger et al. |
| 6,251,090 B1 | 6/2001 | Avery et al. |
| 6,264,971 B1 | 7/2001 | Darougar et al. |
| 6,281,192 B1 | 8/2001 | Leahy et al. |
| 6,375,972 B1 | 4/2002 | Guo et al. |
| 6,416,777 B1 | 7/2002 | Yaacobi |
| 6,478,783 B1 | 11/2002 | Moorehead |
| 6,519,569 B1 | 2/2003 | White et al. |
| 6,520,936 B1 | 2/2003 | Mann |
| 6,527,744 B1 | 3/2003 | Kriesel et al. |
| 6,537,268 B1 | 3/2003 | Gibson et al. |
| 6,564,087 B1 | 5/2003 | Pitris et al. |
| 6,669,950 B2 | 12/2003 | Yaacobi |
| 6,713,081 B2 | 3/2004 | Robinson et al. |
| 6,719,750 B2 | 4/2004 | Varner et al. |
| 6,852,106 B2 | 2/2005 | Watson et al. |
| 6,962,580 B2 | 11/2005 | Adams et al. |
| 6,976,974 B2 | 12/2005 | Houde et al. |
| 7,070,577 B1 | 7/2006 | Haller et al. |
| 7,191,011 B2 | 3/2007 | Cantlon |
| 7,276,050 B2 | 10/2007 | Franklin |
| 7,637,897 B2 | 12/2009 | Ginggen |
| 8,025,639 B2 | 9/2011 | Powers et al. |
| 8,177,762 B2 | 5/2012 | Beasley et al. |
| 8,202,259 B2 | 6/2012 | Evans et al. |
| 8,348,897 B2 | 1/2013 | Shih et al. |
| 9,050,407 B2 | 6/2015 | Shih et al. |
| 2002/0040208 A1 | 4/2002 | Flaherty et al. |
| 2002/0103412 A1 | 8/2002 | Trimmer |
| 2002/0128604 A1 | 9/2002 | Nakajima |
| 2002/0188282 A1 | 12/2002 | Greenberg |
| 2003/0014036 A1 | 1/2003 | Varner et al. |
| 2003/0040479 A1* | 2/2003 | Demopulos ........ A61K 31/4436 514/18.4 |
| 2003/0064088 A1 | 4/2003 | Carvalho et al. |
| 2003/0069560 A1 | 4/2003 | Adamis et al. |
| 2003/0078195 A1* | 4/2003 | Kristensen et al. ............. 514/3 |
| 2003/0141618 A1 | 7/2003 | Braithwaite et al. |
| 2004/0028655 A1 | 2/2004 | Nelson et al. |
| 2004/0143221 A1 | 7/2004 | Shadduck |
| 2004/0199130 A1 | 10/2004 | Chornenky et al. |
| 2005/0175708 A1 | 8/2005 | Carrasquillo et al. |
| 2005/0187515 A1 | 8/2005 | Varrichio et al. |
| 2005/0208103 A1 | 9/2005 | Adamis et al. |
| 2006/0089619 A1 | 4/2006 | Ginggen |
| 2006/0167435 A1 | 7/2006 | Adamis et al. |
| 2006/0235428 A1 | 10/2006 | Silvestrini |
| 2006/0258994 A1 | 11/2006 | Avery |
| 2006/0259015 A1 | 11/2006 | Steinbach |
| 2006/0264897 A1 | 11/2006 | Lobl et al. |
| 2007/0021735 A1 | 1/2007 | Bhavaraju et al. |
| 2007/0078391 A1 | 4/2007 | Wortley et al. |
| 2007/0112328 A1 | 5/2007 | Steinbach et al. |
| 2007/0255235 A1 | 11/2007 | Olsen et al. |
| 2007/0255261 A1 | 11/2007 | Haase |
| 2008/0039792 A1 | 2/2008 | Meng et al. |
| 2008/0045930 A1* | 2/2008 | Makin et al. .............. 604/890.1 |
| 2008/0181930 A1 | 7/2008 | Rodstrom et al. |
| 2008/0234637 A1 | 9/2008 | McConnell et al. |
| 2008/0314978 A1* | 12/2008 | Fedorko ................. G06Q 10/08 235/385 |
| 2009/0028824 A1 | 1/2009 | Chiang et al. |
| 2009/0088732 A1* | 4/2009 | Villegas .................... 604/891.1 |
| 2009/0118683 A1 | 5/2009 | Hanson et al. |
| 2009/0192493 A1 | 7/2009 | Meng et al. |
| 2009/0227855 A1* | 9/2009 | Hill et al. .................... 600/365 |
| 2009/0240241 A1 | 9/2009 | Hyde et al. |
| 2009/0306595 A1 | 12/2009 | Shih et al. |
| 2010/0004639 A1* | 1/2010 | Pang et al. ................. 604/891.1 |
| 2010/0277316 A1 | 11/2010 | Schlangen et al. |
| 2012/0234433 A1 | 9/2012 | Shih et al. |
| 2013/0102962 A1 | 4/2013 | Shih et al. |
| 2013/0116664 A1 | 5/2013 | Tai et al. |
| 2013/0116665 A1 | 5/2013 | Humayun et al. |
| 2013/0226105 A1 | 8/2013 | Hyde et al. |
| 2013/0289482 A1 | 10/2013 | Meng et al. |

FOREIGN PATENT DOCUMENTS

| | | |
|---|---|---|
| CN | 1321096 A | 11/2001 |
| CN | 102202706 A | 9/2011 |
| CN | 103349803 A | 10/2013 |
| CN | 103394142 A | 11/2013 |
| CN | 103608054 A | 2/2014 |
| DE | 3915708 A1 | 2/1990 |
| DE | 3390255 C2 | 6/1992 |
| DE | 4436540 A1 | 4/1996 |
| DE | 202004008151 U1 | 11/2005 |
| EP | 0251680 A2 | 1/1988 |
| EP | 0646381 A1 | 4/1995 |
| EP | 1649884 A1 | 4/2006 |

(56) References Cited

FOREIGN PATENT DOCUMENTS

| | | | |
|---|---|---|---|
| EP | 2240220 A2 | 10/2010 |
| EP | 2266643 A2 | 12/2010 |
| EP | 2266643 A3 | 3/2011 |
| EP | 2320972 A2 | 5/2011 |
| EP | 2686038 A1 | 1/2014 |
| EP | 2727616 A1 | 5/2014 |
| EP | 2760504 A2 | 8/2014 |
| FR | 2091189 A5 | 1/1972 |
| GB | 1345764 A | 2/1974 |
| GB | 1345764 A | 2/1974 |
| IE | 38474 L | 6/1973 |
| JP | 2-191468 A | 7/1990 |
| JP | 2002-529185 A | 9/2002 |
| JP | 3503852 B2 | 3/2004 |
| JP | 2004-535886 A | 12/2004 |
| JP | 2005-131414 A | 5/2005 |
| JP | 2005-521433 A | 7/2005 |
| JP | 2006-501014 A | 1/2006 |
| JP | 2006-526430 A | 11/2006 |
| JP | 2011-509120 A | 3/2011 |
| JP | 2014-028145 A | 2/2014 |
| WO | 1984/001718 A1 | 5/1984 |
| WO | WO-95013838 A1 | 5/1995 |
| WO | WO-99017749 A1 | 4/1999 |
| WO | WO-99038552 A1 | 8/1999 |
| WO | WO-99062576 A1 | 12/1999 |
| WO | WO-00026367 A2 | 5/2000 |
| WO | WO-00040089 A1 | 7/2000 |
| WO | WO-200074751 A1 | 12/2000 |
| WO | WO-01012158 A1 | 2/2001 |
| WO | WO-01056634 A1 | 8/2001 |
| WO | WO-01066173 A1 | 9/2001 |
| WO | WO-01094784 A1 | 12/2001 |
| WO | WO-2002040208 A1 | 5/2002 |
| WO | WO-03002170 A2 | 1/2003 |
| WO | 2003/009774 A2 | 2/2003 |
| WO | 2003/009784 A1 | 2/2003 |
| WO | WO-03024360 A1 | 3/2003 |
| WO | WO-04014969 A1 | 2/2004 |
| WO | WO-04066871 A2 | 8/2004 |
| WO | 2004/073765 A2 | 9/2004 |
| WO | WO-04073551 A2 | 9/2004 |
| WO | WO-05046769 A2 | 5/2005 |
| WO | WO-06012280 A1 | 2/2006 |
| WO | WO-06014793 A1 | 2/2006 |
| WO | WO-06075016 A1 | 7/2006 |
| WO | 2006/096686 A1 | 9/2006 |
| WO | 2006/114638 A2 | 11/2006 |
| WO | WO-07084765 A2 | 7/2007 |
| WO | WO-07106557 A2 | 9/2007 |
| WO | WO-2009137777 A2 | 11/2009 |
| WO | WO-2011022484 A1 | 2/2011 |
| WO | 2012/125695 A1 | 9/2012 |
| WO | 2013/052414 A2 | 4/2013 |
| WO | 2013/052414 A3 | 6/2013 |

OTHER PUBLICATIONS

"The Optimed Advantage—Glaucoma Pressure Regulator", Optimed Advertising Brochure, Journal of Glaucoma, vol. 2, No. 3, 1993, 4 pages.

European Patent Application No. 07753177.0, European Office Action dated Jan. 29, 2009, 6 pages.

European Patent Application No. 07753177.0, European Office Action dated Feb. 5, 2010, 3 pages.

European Patent Application No. 09701298.3, European Office Action dated Jan. 29, 2013, 5 pages.

European Patent Application No. 09701298.3, European Search Report dated Mar. 1, 2011, 11 pages.

International Patent Application No. PCT/US2007/006530, International Search Report and Written Opinion dated Nov. 12, 2007, 15 pages.

International Patent Application No. PCT/US2007/006530, Invitation to Pay Additional Fees and Partial International Search dated Jul. 31, 2007, 7 pages.

International Patent Application No. PCT/US2008/087690, International Search Report and Written Opinion dated Aug. 11, 2009, 15 pages.

International Patent Application No. PCT/US2008/087690, Invitation to Pay Additional Fees and Partial International Search dated May 15, 2009, 5 pages.

International Patent Application No. PCT/US2009/030019, International Search Report and Written Opinion dated Jul. 20, 2009, 16 pages.

International Patent Application No. PCT/US2009/030019, Invitation to Pay Additional Fees and Partial International Search dated Jun. 5, 2009, 5 pages.

International Patent Application No. PCT/US2009/043313, International Search Report and Written Opinion dated Feb. 25, 2010, 16 pages.

International Patent Application No. PCT/US2009/043313, Invitation to Pay Additional Fees and Partial International Search dated Nov. 16, 2009, 6 pages.

International Patent Application No. PCT/US2009/043317, International Search Report and Written Opinion dated Feb. 16, 2010, 15 pages.

International Patent Application No. PCT/US2009/043317, Invitation to Pay Additional Fees and Partial International Search dated Nov. 16, 2009, 5 pages.

International Patent Application No. PCT/US2009/043325, International Search Report and Written Opinion dated Nov. 12, 2009, 18 pages.

International Patent Application No. PCT/US2012/029029, International Preliminary Report on Patentability dated Sep. 26, 2013, 9 pages.

Chen et al., "Floating-Disk Parylene Micro Check Valve", Micro Electro Mechanical Systems, MEMS, IEEE 20th International Conference, Jan. 21-25, 2007, pp. 453-456.

Chen et al., "Floating-Disk Parylene Microvalve for Self-Regulating Biomedical Flow Controls", Micro Electro Mechanical Systems, MEMS, IEEE 21st International Conference, Jan. 13-17, 2008, pp. 575-578.

Chen et al., "Surface-Micromachined Parylene Dual Valves for On-Chip Unpowered Microflow Regulation", Journal of Microelectromechanical Systems, vol. 16, No. 2, Apr. 2007, pp. 223-231.

Choudhri et al., "A Comparison of Dorzolamide-Timolol Combination Versus the Concomitant Drugs", American Journal of Ophthalmology, vol. 130, No. 6, Dec. 2000, pp. 832-833.

Durham, N.C., "FDA Approves an Industry First!—The MED-EL Cochlear Implant System is FDA Approved for Use With Magnetic Resonance Imaging (MRI)", PR Newswire, Jun. 18, 2003, 3 pages.

Eliason et al., "An Ocular Perfusion System", Investigate Ophthalmology Visual Science, vol. 19, No. 1, Jan. 1980, pp. 102-105.

Hashizoe et al., "Scleral Plug of Biodegradable Polymers for Controlled Drug Release in the Vitreous", Arch Ophthalmology, vol. 112, No. 10, Oct. 1994, pp. 1380-1384.

Jabs, Douglas A., "Treatment of Cytomegalovirus Retinitis—1992", Arch Ophthalmology, vol. 110, No. 2, Feb. 1992, pp. 185-187.

Khouri et al., "Use of Fixed-Dose Combination Drugs for the Treatment of Glaucoma", Drugs & Aging, vol. 24, No. 12, Dec. 2007, pp. 1007-1016.

Kimura et al., "A New Vitreal Drug Delivery System Using an Implantable Biodegradable Polymeric Device", Investigative Ophthalmology & Visual Science, vol. 35, No. 6, May 1994, pp. 2815-2819.

Lo et al., "A Refillable Polymer Drug Delivery Device for Treatment of Ocular Diseases", The Royal Society of Chemistry, Jan. 1, 2007, 28 pages.

Michelson et al., "Experimental EndophtalmitisTreated With an Implantable Osmotic Minipump", Arch. Ophthalmology, vol. 97, Jul. 1979, pp. 1345-1346.

Miki et al., "A Method for Chronic Drug Infusion Into the Eye", Japanese Journal of Ophthalmology, vol. 28, No. 2, 1984, pp. 140-146.

(56) References Cited

OTHER PUBLICATIONS

Pincus et al., "Why are Only 50% of Courses of Anti-Tumor Necrosis Factor Agents Continued for Only 2 Years in Some Settings? Need for Longterm Observations in Standard Care to Compliment Clinical Trials", Journal of Reumatology, vol. 33, No. 12, Dec. 2006, pp. 2372-2375.
Pope et al., "MRI in Patients with High-Grade Gliomas Treated with Bevacizumab and Chemotherapy", Neurology, vol. 66, No. 8, Apr. 2006, pp. 1258-1260.
Rubsamen et al., "Prevention of Experimental Proliferative Vitreoretinopathy With a Biodegradable Intravitreal Implant for the Sustained Release of Fluorouracil", Arch. Ophthalmology, vol. 112, No. 3, Mar. 1994, pp. 407-413.
Sanborn et al., "Sustained-Release Ganciclovir Therapy for Treatment of Cytomegalovirus Retinitis", Arch Ophthmology, vol. 110, No. 2, Feb. 1992, pp. 188-195.
Smith et al., "Intravitreal Sustained-Release Ganciclovir", Arch Ophthlmology, vol. 110, No. 2, Feb. 1992, pp. 255-258.
Stark-Vance, "Bevacizumab and CPT-11 in the Treatment of Relapsed Malignant Glioma", Neuro Oncology, vol. 7, No. 3, Abstract from the World Federation of Neuro-Oncology Second Quadrennial Meeting and Sixth Meeting of the European Association for Neuro-Oncology, May 5-8, 2005, Abstract 342, Jul. 2005, p. 369.
Steyer, Robert, "Alcon Eye-Drug Setback Raises the Stakes", Available online at <http://www.thestreet.com/story/10187873/1/alcon-eye-drug-setback-raises-the-stakes.html>, Oct. 14, 2004, 4 pages.
Strohmaier et al., "The Efficacy and Safety of the Dorzolamide-Timolol Combination Versus the Concomitant Administration of its Components", Ophthalmology, vol. 105, No. 10, Oct. 1998, pp. 1936-1944.
Xie et al., "An Electrochemical Pumping System for On-Chip Gradient Generation", Analytical Chemistry, vol. 76, No. 13, May 2004, pp. 3756-3763.
International Search Report for PCT/US2012/029029, issued on Jul. 18, 2012 and dated Jul. 26, 2012.
International Search Report and Written Opinion for International Application No. PCT/US2012/058286, issued on Mar. 26, 2013 and dated Apr. 5, 2013.
Examination Report Received for European Patent Application No. 09743763.6 dated Feb. 6, 2015, 4 pages.
Examination Report Received for Chinese Patent Application No. 201310157066.7 dated Oct. 29, 2014, 10 pages (4 pages of English Translation & 6 pages of Official copy).
Examination Report Received for Chinese Patent Application No. 201280013608.7 dated Dec. 17, 2014, 16 pages (8 pages of English Translation & 8 pages of Official copy).
Examination Report Received for Mexican Patent Application No. MX/a/2010/007382 dated Sep. 30, 2013.
Examination Report Received for European Patent Application No. 09701298.3, dated Jan. 29, 2013, 5 pages.
Examination Report Received for European Patent Application No. 10008072.0, dated Jun. 17, 2013, 6 pages.
Examination Report Received for Australian Patent Application No. 2012230033, dated Jul. 9, 2014, 4 pages.
Examination Report Received for European Patent Application No. 09743763.6, dated Sep. 9, 2014, 3 pages.
Extended European Search Report received for Application No. 14152346.4, dated Apr. 9, 2014, 6 pages.
Examination Report Received for Japanese Patent Application No. 2013-157652, dated Jul. 29, 2014, 3 pages.
Examination Report Received for Japanese Patent Application No. 2013-243564, dated Sep. 18, 2014, 7 pages (4 pages of English Translation and 3 pages of Official copy).
Examination Report Received for Mexican Patent Application No. MX/1/2010/012212, dated Mar. 3, 2014.
Examination Report Received for Mexican Patent Application No. MX/1/2010/012212, dated Jun. 5, 2014, 1 page.
Examination Report Received for Mexican Patent Application No. MX/A/2010/007382, dated May 30, 2014.
PCT International Patent Application No. PCT/US2012/58286, International Preliminary Report on Patentability dated Apr. 10, 2014, 10 pages.

\* cited by examiner

IMPLANTABLE DRUG PUMPS AND REFILL DEVICES THEREFOR

CROSS-REFERENCES TO RELATED APPLICATIONS

This application claims priority to and the benefit of U.S. Provisional Patent Application No. 61/541,723, filed on Sep. 30, 2011, and is Continuation-in-Part of U.S. patent application Ser. No. 13/419,968, filed on Mar. 14, 2012, which claims priority to U.S. Provisional Patent Application No. 61/452,399, filed on Mar. 14, 2011. The entire disclosures of all applications are hereby incorporated herein by reference.

BACKGROUND

Medical treatment often requires the administration of a therapeutic agent to a particular part of a patient's body. Some maladies, however, are difficult to treat with currently available therapies and/or require administration of drugs to anatomical regions which are difficult to access. A patient's eye is a prime example of a difficult-to-reach anatomical region, and conventional approaches to treating many vision-threatening diseases, including retinitis pigmentosa, age-related macular degeneration (AMD), diabetic retinopathy, and glaucoma, have associated complications. For example, oral medications can have systemic side effects; topical applications may sting and engender poor patient compliance; injections generally require a medical visit, can be painful, and risk infection; and sustained-release implants must typically be removed after their supply is exhausted. Another example is the chemotherapeutic treatment of cancer, such as breast cancer or meningiomas, which often requires large doses of highly toxic chemotherapeutic agents, such as rapamycin, bevacizumab (e.g., AVASTIN), or irinotecan (CPT-11), to be administered to the patient intravenously, which may result in numerous undesired side effects outside the targeted area.

Implantable drug-delivery devices with refillable drug reservoirs address and overcome many of the problems associated with conventional drug-delivery modalities. They generally facilitate controlled delivery of pharmaceutical solutions to a specified target, and, as the contents of the drug reservoir deplete, allow a physician to refill the reservoir in situ, i.e., while leaving the device implanted within the patient's body. The administration and maintenance benefits that such pump devices afford, however, can also create new or increased hazards to the patient. Care must be taken to prevent the pump from being refilled with the wrong drug (e.g., a drug with the wrong active ingredient or a non-proprietary formulation), for example. Typically, the refill drug should match the previously administered drug. In addition, refilling the implanted drug pump device often entails a need to reprogram the device, e.g., to adjust a dosage protocol in response to a change in the patient's condition; this step may be overlooked or mishandled.

It would be desirable, therefore, to ensure that refill of implanted drug pump devices is accomplished in a manner that automatically verifies proper drug selection and that, further, ensures proper and convenient entry of program and/or information updates to the implanted devices during the course of the refill procedure.

SUMMARY

In various embodiments, the present invention relates to implantable drug pump devices and systems for refilling them and facilities for establishing communication between the refill system and the implanted device. The refill system generally includes a needle insertable into a fill port of the implanted device and fluidically connectable to a drug cartridge or similar container, a pump for causing fluid flow from the cartridge into the drug reservoir of the implanted device, electronic circuitry for controlling pump operation, and a communication module that facilitates wireless communication between the electronic circuitry and the implanted device. In some embodiments, the communication module is provided in a handheld telemetry wand connected to a base unit of the refill system. Via the wireless link, the drug pump device and refill system can exchange data such as, for example, refill information (including, e.g., a type of drug), a drug pump device history, a drug dosage log, and/or a drug-delivery protocol. Further, the refill system can facilitate reprogramming the implanted device wirelessly.

The refill system may also be able to electronically read an optical ID, barcode, RFID "tag," or other electronically or optically readable label on the drug cartridge that indicates the drug stored therein. (The term "electronically reading," as used herein, means that the label is interrogated automatically by an electric, magnetic, optical, or other suitable type of sensor, and the signal acquired thereby is electronically processed to infer the drug type (or other encoded information). Thus, "electronically reading" does not limit the initial information-acquisition process to electronic modalities, but merely indicates that electronic data processing is used in the overall process of obtaining and utilizing information from the label. The label may, for example, be scanned by an optical sensor, and the optical signal may thereafter be converted into an electronic signal.) Using the information from the label, in conjunction with an indication of the refill drug required by the drug pump device (which may, e.g., be the same drug as was previously administered by the device), the refill system can automatically ensure that the proper drug is being injected. In some embodiments, the refill system also provides a communication link to an external server, where data for many patients and implanted devices may be aggregated—e.g., in association with the serial numbers of the respective devices—for individualized retrieval (to facilitate proper treatment of a particular patient) or for analysis across a patient population. Such central data storage provides the flexibility to refill and reprogram the drug pump device with any refill system in accordance herewith, as long as communication with the central server can be established.

Accordingly, in one aspect, the invention provides a system for filling an implanted, refillable drug pump device including a drug reservoir with a fill port. The system includes a needle for insertion into the fill port of the drug pump device and fluidically connectable to one or more fluid containers, one or more pumps for causing fluid flow through the needle between the fluid container(s) and the drug reservoir, electronic circuitry including a processor for controlling operation of the pump(s), and a wireless communication module facilitating wireless data exchange between the electronic circuitry and the implanted drug pump device. The system may further include tubing for fluidically connecting the fluid container(s) to the needle.

In some embodiments, the wireless communication module is integrated in the electronic circuitry. In alternative embodiments, the wireless communication module is integrated in a handheld telemetry wand or patient-worn eyeglasses in communication with the electronic circuitry. The electronic circuitry may be configured to control pump operation based, at least in part, on data received from the implanted drug pump device via the wireless communication module. The data may include, for example, sensor readings of sensors disposed in the drug reservoir, information indicative of a type of drug to be administered, and/or information indicative of an error condition that has occurred in the drug pump device since a previous communication between the electronic circuitry and the drug pump device. The electronic circuitry may also be configured to control pump operation based, at least in part, on sensor readings of sensors disposed in the needle, the pump(s), and/or a fluidic connection between the needle and the fluid container(s).

In some embodiments, the wireless communication module is configured to send refill information to the implanted drug pump device for storage therein, and/or to retrieve refill information previously stored in the implanted drug pump device. Operation of the drug pump device may be based, at least in part, on the refill information. The refill information may include, e.g., a type of drug, an amount of drug, a dosing schedule, or a refill date.

The one or more fluid containers may include a drug-containing cartridge and, in some embodiments, further a waste-fluid receptacle and/or a rinsing-fluid-containing cartridge. The drug-containing cartridge may have a label—e.g., in the form of a barcode, an RFID, an optical ID, or an EPROM—indicative of a type of drug contained in the cartridge. The refill system may include a reader for reading the label. Alternatively or additionally, the drug-containing cartridge may have a shape indicative of a type of drug contained in the cartridge. In some embodiments, the electronic circuitry activates the pump to cause fluid flow from the drug-containing cartridge to the drug reservoir only if the type of drug indicated by the label matches a type of drug to be administered as determined based on data received from the implanted drug pump device via the wireless communication module.

In some embodiments, the electronic circuitry of the refill system also facilitates data exchange with an external server. The data exchanged with the external server may, e.g., include a serial number of the implanted drug pump device (as received by the system from the implanted drug pump device via the wireless communication module) and data associated therewith. The data associated with the serial number of the implanted drug pump device may include, for example, patient data, a drug dosage log, and/or a drug pump device history.

In another aspect, the invention is directed to a refill system (for filling a drug reservoir of an implanted, refillable drug pump device via a fluidic connection between a drug-containing cartridge and a fill port in the drug reservoir) that includes a base unit and, in communication therewith, a wireless communication module facilitating wireless data exchange with the implanted drug pump device. The base unit includes a pump for causing fluid flow through the fluidic connection between the drug-containing cartridge and the drug reservoir, and electronic circuitry (including a processor) for controlling operation of the pump.

In yet another aspect, the invention provides a method of verifying proper selection of a drug prior to injection of the drug by a refill system into the drug reservoir of an implanted drug pump device. The method involves receiving a drug cartridge having an electronically readable label indicative of a drug contained therein in a well of the refill system, causing the refill system to electronically read the label, causing the refill system to receive (from the implanted drug pump device via a wireless communication module of the refill system) data indicative of a drug to be administered, and causing the refill system to determine whether the drug indicated by the label matches the drug to be administered. If so, the refill system injects the drug into the reservoir.

BRIEF DESCRIPTION OF THE DRAWINGS

The foregoing will be more readily understood from the following detailed description of the invention, in particular, when taken in conjunction with the drawings, in which.

DETAILED DESCRIPTION

The present invention relates, generally, to implantable drug pump devices with refillable drug reservoirs, as well as to apparatus, systems, and methods that facilitate the refill process. Various embodiments described herein relate specifically to drug pump devices implanted into the eye (e.g., between the sclera and conjunctiva); however, many features relevant to such ophthalmic pumps are also applicable to other drug pump devices, such as, e.g., implantable insulin pumps. Accordingly, where reference to the eye is made in the following description, or in the figures, such reference is generally intended to be merely illustrative, and not as limiting the scope of the invention.

Figure 1:
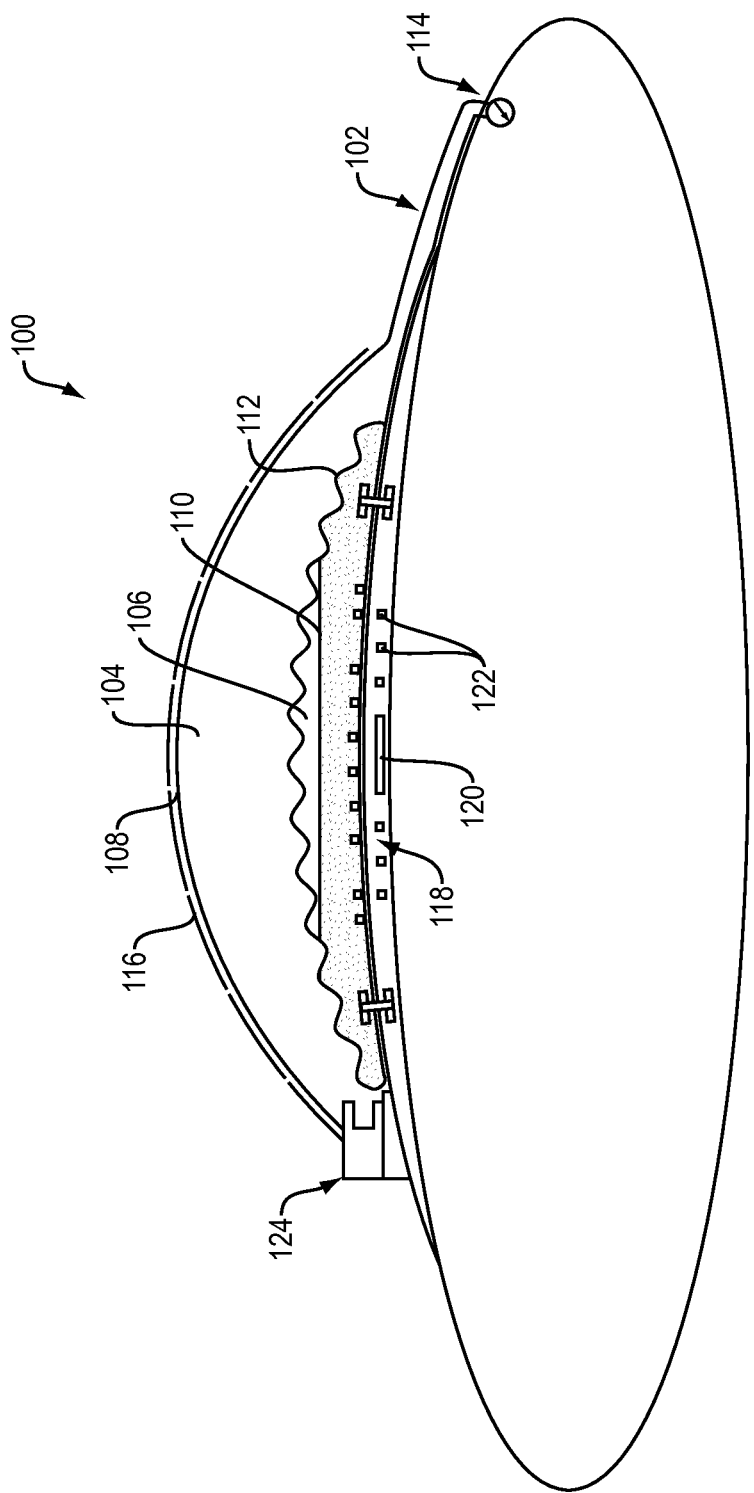
FIG. 1 is a side view of an implantable, refillable drug pump device in accordance with various embodiments of the invention.

FIG. 1 illustrates an exemplary electrolytically driven drug pump device 100 in accordance herewith (described in detail in U.S. patent application Ser. No. 12/463,251, the entire disclosure of which is hereby incorporated by reference). The drug pump device 100 includes a cannula 102 and a pair of chambers 104, 106 bounded by an envelope 108. The top chamber 104 defines a drug reservoir that contains the drug to be administered in liquid form, and the bottom chamber 106 contains a liquid which, when subjected to electrolysis using electrolysis electrodes 110, evolves a gaseous product. The two chambers are separated by a corrugated diaphragm 112. The cannula 102 connects the top drug chamber 104 with a check valve 114 inserted at the site of administration. The envelope 108 resides within a shaped protective shell 116 made of a flexible material (e.g., a bladder or collapsible chamber) or a relatively rigid biocompatible material (e.g., medical-grade polypropylene). Control circuitry 118, a battery 120, and an induction coil 122 for power and data transmission are embedded between the bottom wall of the electrolyte chamber 106 and the floor of the shell 116. Depending on the complexity of the control functionality it provides, the control circuitry 118 may be implemented, e.g., in the form of analog circuits, digital integrated circuits (such as, e.g., microcontrollers), or programmable logic devices. In some embodiments, the control circuitry 118 includes a microprocessor and associated memory for implementing complex drug-delivery protocols. The drug pump device 100 may also include various sensors (e.g., pressure and flow sensors) for monitoring the status and operation of the various device components, and such data may be logged in the memory for subsequent retrieval and review.

Implantable, refillable drug pump devices need not, of course, have the particular configuration depicted in FIG. 1. Various modifications are possible, including, e.g., devices in which the drug reservoir and pump chamber are arranged side-by-side (rather than one above the other), and/or in which pressure generated in the pump chamber is exerted on the drug reservoir via a piston (rather than by a flexible diaphragm). Furthermore, the pump need not in all embodiments be driven electrolytically, but may exploit, e.g., osmotic or electroosmotic drive mechanisms, or even pressure generated manually.

Importantly for the prolonged use of the drug pump device 100 following implantation, the device 100 includes one or more ports 124 in fluid communication with the drug reservoir 104, which permit a refill needle (not shown) to be inserted therethrough. The refill port 124 may define an aperture through the wall of the reservoir 104, which may be closed and sealed with a septum or plug made of a puncturable, self-sealing material, allowing a non-coring needle (e.g., a needle that does not remove any of the material it punctures) to pierce through the septum while ensuring that the septum reseals itself, or "heals," upon removal of the needle. Preferably, the self-sealing material is biocompatible and able to withstand multiple punctures by the needle. The septum or plug may be made of any of a variety of elastomeric polymers (such as, e.g., silicone, polydimethylsiloxane (PDMS), polyurethane, polyethylene, parylene C, or rubber), and the specific composition of the polymer mixtures may be chosen so as to enhance the self-sealing properties. Silicone, for example, is naturally self-healing, but this property is more pronounced in particular formulations well-known to persons of skill in the art. The septum material may be injected directly into the aperture of the port and cured in place. In some embodiments, a slit is preformed in the septum, and the needle is inserted along this slit; the septum and surrounding port walls are sized such that radial pressure from the walls of the port compresses the septum and, with it, the slit, preventing leakage during filling and after the needle has been removed.

Figure 2A:
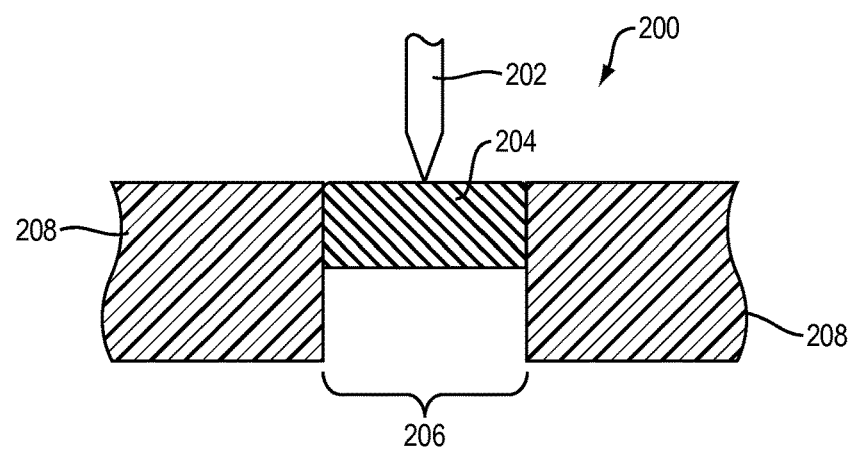
FIGS. 2A-2H are side views of refill ports in accordance with various embodiments of the invention.
Figure 2B:
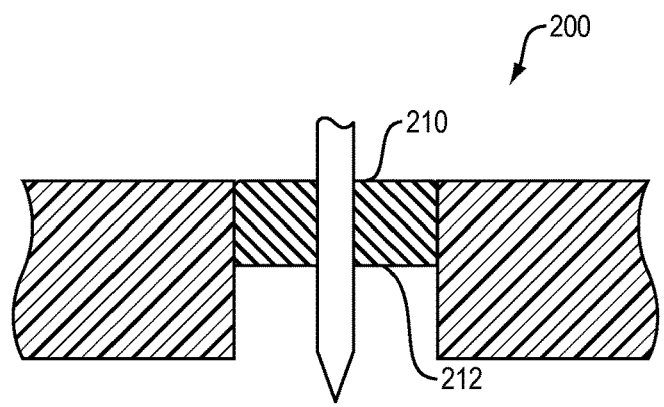
Figure 2C:
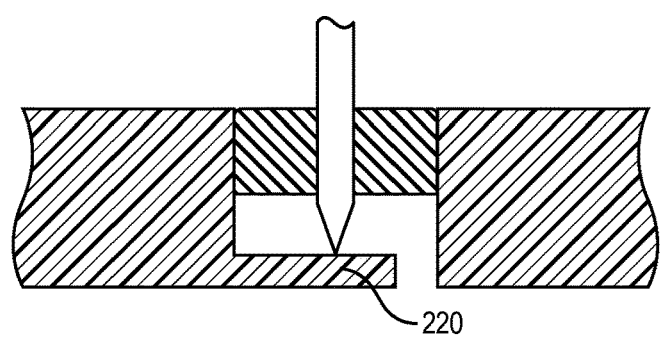
Figure 2D:
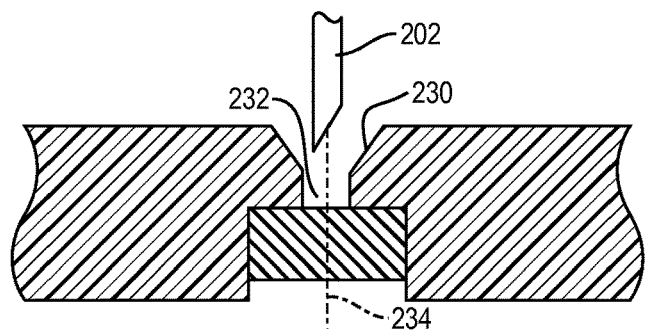
Figure 2E:
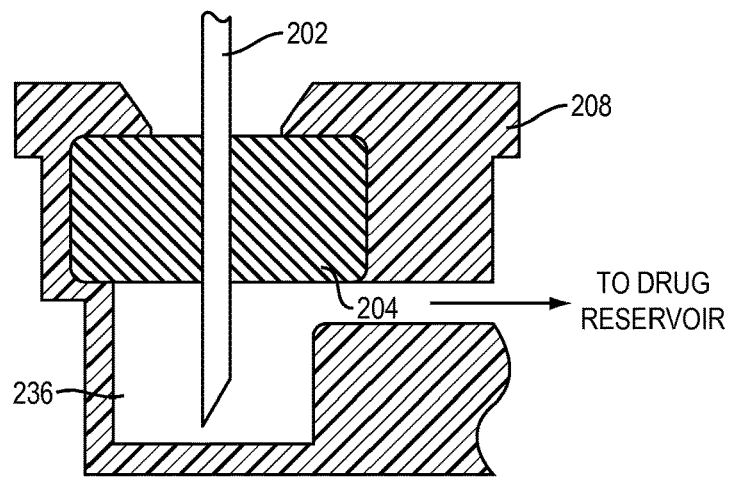

FIGS. 2A and 2B provide close-up views of a simple refill port 200 before and after, respectively, insertion of the needle 202. As shown, the septum 204 need only partially extend through the aperture 206 in the reservoir wall 208, and may form a single block of material with flat needle entry and exit surfaces 210, 212. FIGS. 2C-2F illustrate various alternative refill port embodiments. For example, the port shown in FIG. 2C includes a needle stop 220 protruding from the side wall of the port at a lower end. Once the needle 202 is inserted sufficiently far to inject fluid into the drug reservoir 104, the needle stop 220 halts further progress of the needle to avoid accidental damage to the drug pump device 100 and/or the patient. FIG. 2D illustrates a port with a conically shaped recess 230 at the entry side merging into a narrow channel portion 232, which collectively serve to guide the needle 202 through the port along a central axis 234. As illustrated in FIG. 2E, the aperture through the reservoir wall 208 need not open directly into the main portion of the drug reservoir 104. Instead, it may open into a port chamber 236 that is fluidically connected to the reservoir 104, e.g., via a fluid channel perpendicular to the needle entry direction. In this embodiment, the bottom wall of the port chamber 236 serves to stop the needle.

Figure 2F:
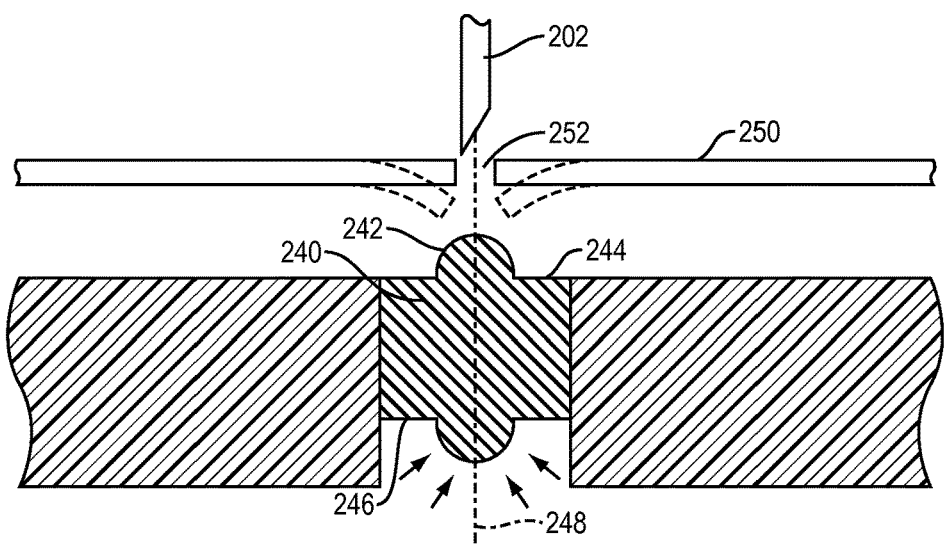

Finally, FIG. 2F shows an embodiment in which the septum 240 includes protuberances 242, or "bumps," on the needle entry and exit surfaces 244, 246, located around the desired puncture sites. These bumps serve to direct pressure exerted at the exit surface 246 (i.e., the interior surface of the reservoir 104) by the liquid drug and at the entry surface 244 by the ambient fluid (e.g., of the surrounding tissue) toward the needle puncture path 248 (i.e., the straight line connecting the desired puncture sites and corresponding to the desired insertion path of the needle). Pressure thus redirected can aid in the self-healing of the septum 240. As shown, the bumps 242 may take substantially semi-spherical form; however, other shapes may also be used to redirect pressure and promote self-healing. Further, the septum 240 need not necessarily have bumps 242 on both sides. FIG. 2F further illustrates use of a separate layer 250 of non-puncturable, flexible material disposed above the aperture through the reservoir wall. The layer 250 has a hole 252 centered above the bumps 242, which serves to guide the needle toward and along the desired insertion path 248. The hole 252 is originally smaller than the cross-section of the needle, but increases in size as pressure exerted by the needle deflects the layer 250 downward, as indicated in the figure by dashed lines. The various features of the refill port may, of course, be used in different combinations. Further embodiments are described, for example, in U.S. patent application Ser. No. 12/463,247, the entire disclosure of which is hereby incorporated by reference.

The ports shown in FIGS. 2A-2F are configured for substantially perpendicular needle insertion. In certain alternative embodiments, however, the refill port 124 is angled with respect to the reservoir wall, both to minimize pain and vitreal reflux and to improve self-healing. Oblique needle-entry paths through the septum can enhance self-sealing performance because, after removal of the needle, external pressure exerted on the septum from both sides acts at an angle to the needle tunnel, tending to collapse it and render its diameter smaller than that of the needle. Orienting the refill port so that needle entry occurs at an angle to the pressure developed by the pump can therefore increase the reliability of the plug or septum in a similar manner as the bumps describe above with respect to FIG. 2F.

Various other arrangements can be used to exploit pressure generated in the drug reservoir 104 (in particular, when the pump device actively pumps) to aid self-healing. In one embodiment, the entry path for the needle remains perpendicular to the surface, but the inside of the refill port is configured so that part of a side of the refill septum is also exposed to pump pressure in order to close any holes through the septum. In another configuration, the septum is larger at the bottom than at the top, and mounted so as to be wedged in a conical bore. The pressure of the pump acts to push the septum up into the bore, resulting in compression of the refill needle holes. The conical shape of the refill port septum also accommodates inaccuracy in the angle of needle insertion. In still another embodiment, the refill plug or septum is configured as a membrane that covers and extends beyond the perimeter of the bore through the reservoir wall. The edges of the septum are bonded to the wall or held with corrugations, with the septum initially convex towards the inside of the bore. When the pump is activated, the pressure acts to push the bulging septum into its containing area, creating lateral pressure that closes any needle holes in the septum. In another design, the bottom of the septum is convex so that pressure conducted into the bore compresses the septum therein, creating lateral pressure that acts to further close the holes. Still another design initially places and maintains the septum under lateral compression, creating a continual closing pressure on any needle paths through the thickness.

Figure 2G:
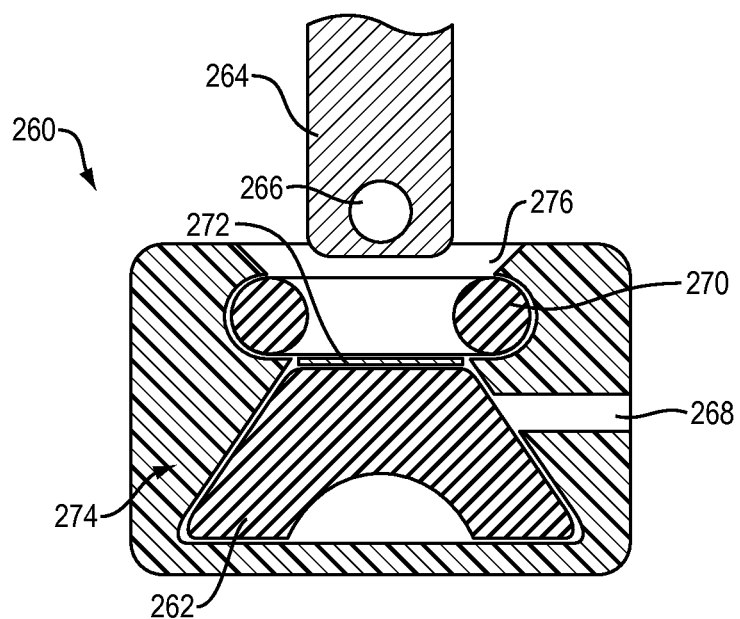
Figure 2H:
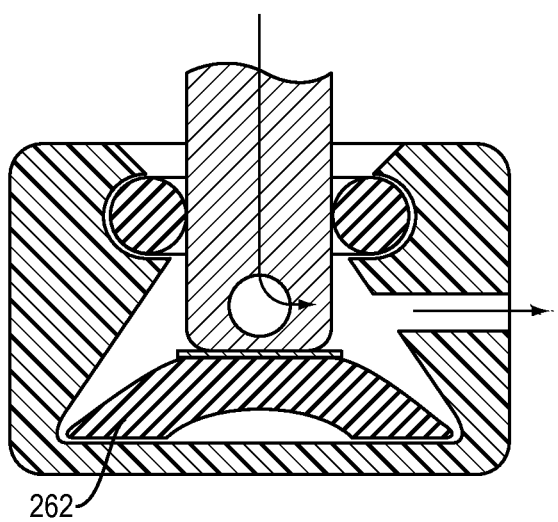

In yet another embodiment, shown in FIGS. 2G and 2H before and after needle insertion, respectively, the needle port 260 is configured so as to entirely avoid the need to pierce the septum or plug 262. Instead, the plug 262 is pushed by a blunt tip needle 264 with an aperture 266 (or "port") in the side wall of the needle tip. When pushed, the plug 262 collapses and clears a fluidic path 268 leading to the drug reservoir 104. When the needle 264 is retracted back, releasing the pressure on the silicone plug 262, the plug 262 returns to its initial shape, closing the fluidic path 268 to the reservoir 104. The plug 262 is typically made of silicone, and may have a convex (viewed from the needle), inverted-bowl shape. The needle 264 is sealed by a silicone O-ring 270 (or, more generally, a second elastomeric septum with a center hole) disposed above the plug 262 to block the leak path of fluid to the outside of the refill port 260. (The O-ring 270 may have, in its uncompressed state, an inner diameter slightly below the needle diameter.) The deformable plug 262 may have a hard, needle-impenetrable plate 272 attached thereto at an upper surface; this hard plate 272 transfers pressure exerted by the needle so as to collapse the plug 262. (Alternatively, the plate may simply be disposed above the plug, without being attached.) The needle port 260 may include a wall structure 274 that is molded or machined into a complex shape defining a layered cavity that accommodates the deformable septum 262 and O-ring 270. The port may also include a guiding disk 276 forming a conical aperture, similar to that shown in FIG. 2D, for guiding the needle 264.

The design of needle port 260 is beneficial in several ways: Since the needle 264 never penetrates the septum 262, the needle 264 need not be non-coring, allowing for larger needle diameters, which, in turn, facilitate more rapid filling of the reservoir 104. Further, there is loose particle rapid fill. Only minimum insertion force is needed, and a larger initial target for the needle prior to penetration is provided.

Figure 3:
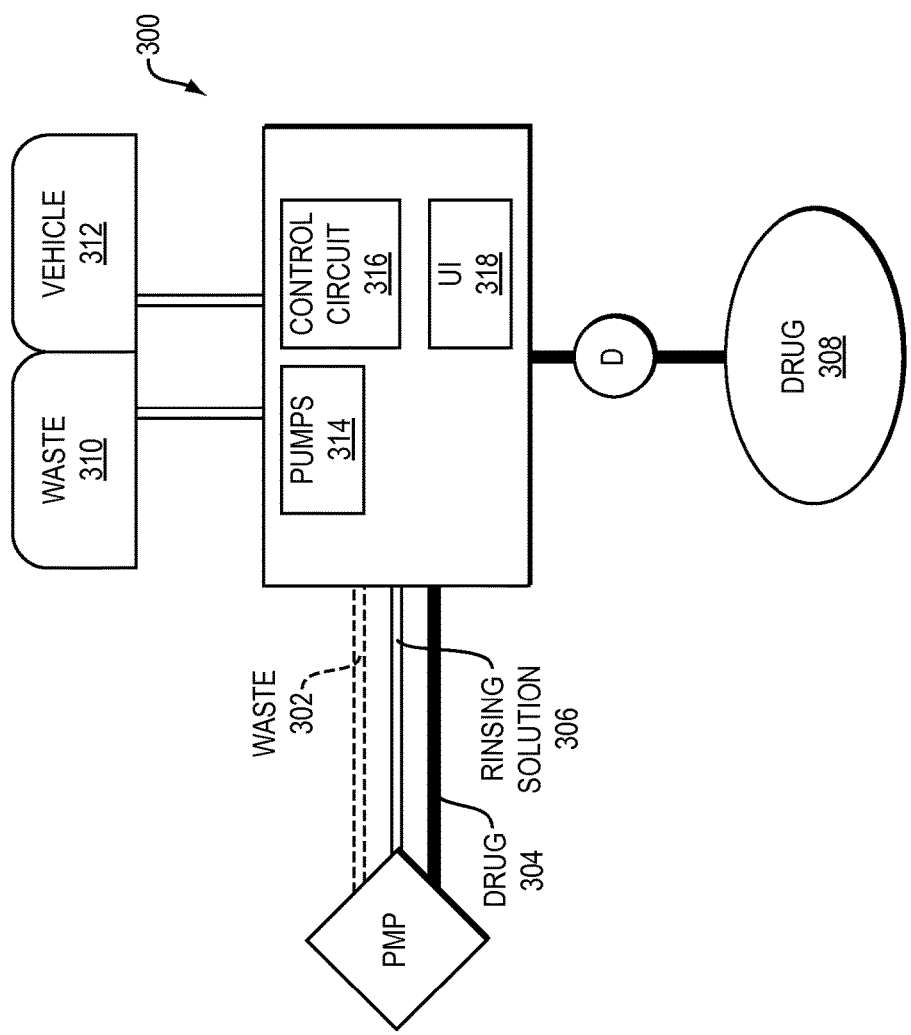
FIG. 3 is a schematic diagram of a refill system in accordance with various embodiments of the invention.

Through the refill port 124, the existing fluid in the reservoir (such as any residual drug) can be removed, the reservoir washed, and a filling/refilling solution injected. Certain embodiments of the invention involve an external refill system that can be interfaced to the drug reservoir for the automatic filling/refilling of the reservoir, as conceptually illustrated in FIG. 3. The refill system 300 generally includes at least two channels: one channel 302 for aspirating fluid (e.g., expired and/or remnant drug) from the reservoir of the drug pump device 100 and another channel 304 for loading new drug into the reservoir. In some embodiments, the system further includes a third channel 306 for rinsing the drug pump prior to filling it with the fresh drug. Each channel is fluidically connectable to a depot or container, e.g., one containing the drug to be dispensed (308), one receiving waste liquid from the drug pump device 100 (310), and one containing the rinsing solution (312). This rinsing solution may be the drug vehicle (e.g., a fluid missing the active ingredient, but otherwise having the same composition as the liquid drug), or any solution compatible with the drug and drug pump device 100.

The refill system 300 also includes one or more pumps 314 for generating positive or negative pressure to effect the infusion and suction of liquid into and out of the drug pump device 100. The pumps 314 may be standard mechanical pumps (e.g., gear, diaphragm, peristaltic, or syringe pumps), or pneumatic systems such as, e.g., vacuum generators, air compressors, pneumatic motors, pneumatic actuators, etc. In some embodiments, pressure sensors, flow sensors, and/or valves are integrated into the channels 302, 304, 306 and/or the pumps 314 to facilitate monitoring of the flow rate and/or pressure during the refilling process and controlling pump operation based thereon. The refill system 300 further includes electronic control circuitry 316 that directs the operation of the pump(s), and/or a user interface 318 that allows a user (e.g., a physician or nurse) to provide input to the control circuitry 316 and/or to manually trigger certain pre-defined pump functions (e.g., via buttons, a foot pedal, and/or a conventional computer user interface including, e.g., a screen, keyboard, and mouse). The electronic control circuitry is conventional and typically comprises a processor for performing computations related to the pump operation. The processor may be a general-purpose or special-purpose processor, and may utilize any of a wide variety of data-processing and control technologies, including, e.g., a microcomputer, mini-computer, mainframe computer, programmed microprocessor, microcontroller, peripheral integrated circuit element, CSIC (customer-specific integrated circuit), ASIC (application-specific integrated circuit), logic circuit, digital signal processor, programmable logic device such as an FPGA (field-programmable gate array) or PLA (programmable logic array), RFID processor, or smart chip.

Figure 4A:
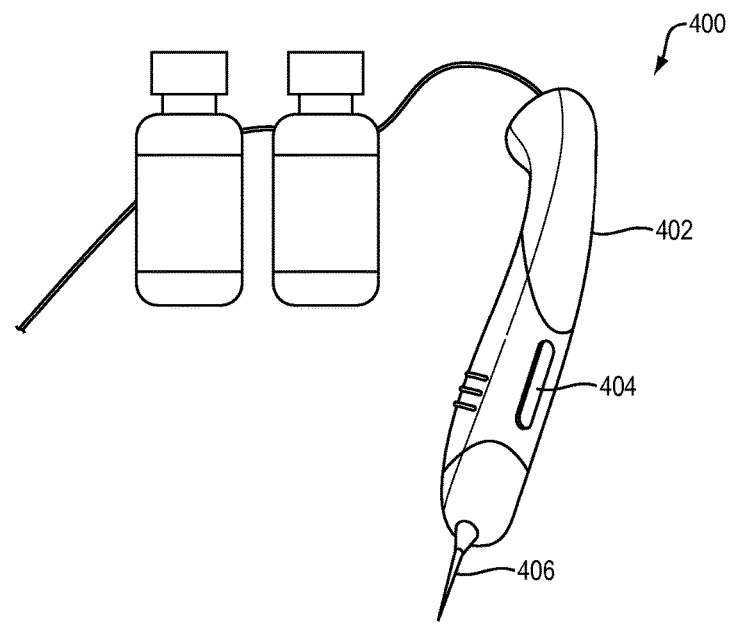
FIGS. 4A and 4B are isometric views of a refill tool and tubing set, respectively, of a refill system in accordance with various embodiments of the invention.

The refill system 300 may be implemented as a single unit or, alternatively, as multiple components. In certain embodiments, the pumps 314, control circuitry 316, and (optionally) valves and sensors are integrated into a reusable base unit, whereas the fluid channels 302, 304, 306 are provided in a replaceable and/or disposable tubing set connectable to the base unit and, at the other end, to a refill needle. The needle is preferably a small-bore needle and may, as shown in FIG. 4A, be integrated into a handheld refill tool 400 including an ergonomic handle portion 402 with a push button, slider, or other mechanically actuable control 404 for extending and/or retracting the needle 406. The refill tool 400 allows a physician to refill the implanted device in situ. In preferred embodiments, the same needle is used during the entire refill process so as to minimize the needle insertion frequency into the drug reservoir and the associated stress for patient and physician as well as the wear on the refill port. A single needle insertion may even suffice if multiple fluids (e.g., multiple separately stored drugs to be administered together) are to be injected into the drug pump device 100. The needle 406 is, thus, sequentially connected to different fluid containers.

Figure 4B:
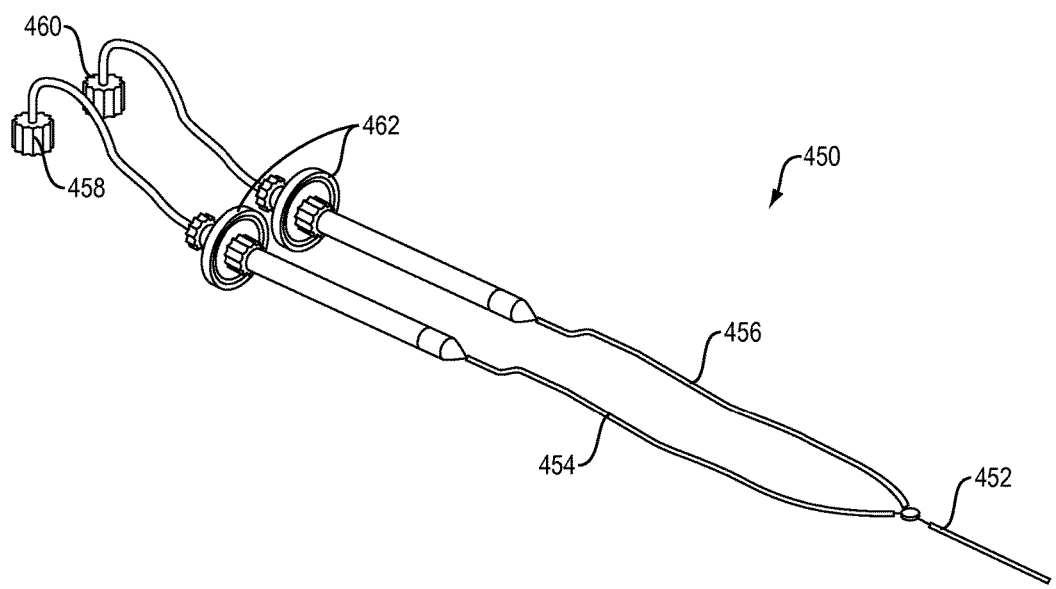

FIG. 4B illustrates an exemplary two-channel tubing set 450 suitable for this purpose. The tubing set 450 branches, from a proximal channel portion 452 connected to the needle 406, into two channels 454, 456 coupled at the distal end, via respective fluidic connectors 458, 460, to the containers providing fluid to or receiving fluid from the reservoir 104 of the implanted device 100. The channels 454, 456 may have one-way valves that allow drug or rinsing fluid from containers 308, 312 to flow via the refill channel 454 to the needle 406 and waste fluid from the reservoir 104 to flow via the aspiration channel 456 to the waste-fluid container 310, but prevent fluid flow in the respective opposite direction. Further, the channels 454, 456 may include sterile filters 462 that prevent air from entering and contaminating the new drug. The same types of filters may also serve to prevent fluid from accidentally entering a vacuum pump, coming into contact with sensors or electronics within the base unit, or otherwise contaminating the drug refill system 300 (e.g., by means of a hydrophobic membrane that allows passage of air, but not an aqueous solution). As a person of skill in the art will readily appreciate, the tubing set 450 can be modified straightforwardly into a three-channel fluidic manifold.

In some embodiments, one or more of the containers 308, 310, 312 holding the drug, waste liquid, and rinsing solution are provided in the form of vials or cartridges (hereinafter used synonymously), and may be sold along with the disposable tubing set 450 in a drug refill kit. The waste-liquid cartridge 310 (or other container) may contain a dye that changes the color of the waste liquid upon contact to a noxious or at least noticeably anomalous hue such as black so as to prevent users from inadvertently re-injecting waste drug back into the patient or pump. The dye may, e.g., consist of natural or synthetic dyestuffs that are contained in the cartridge in powder form or line the surface of the cartridge. Furthermore, the cartridge 310 may contain reactive agents that disable use of the drug by destroying its activity, e.g., via an acid-base reaction, but which are non-toxic so as to avoid harm to the patient should the mixture be re-injected.

The base unit or refill tool of the refill system 300 may have receiving wells or other receptacles for the cartridges 308, 310, 312. In certain embodiments, the cartridges have a proprietary shape that must mate with a complementary receiving well in the refill system. This approach can also facilitate mechanical locking of the cartridge to the drug refill system, e.g., so that it snaps into place. Mechanical locking may be accomplished, e.g., using a trapezoid, triangle, or hexagonal male connector on the drug refill system and a geometrically complementary connector on the cartridge. Using cartridges of a particular shape in conjunction with matching receiving wells may serve to prevent non-proprietary cartridges or drugs from being used with the refill system 300, e.g., to ensure the integrity of the drug. A further level of security may be obtained by facilitating electronic communication between the cartridge and the refill system 300. For example, the cartridge may have a barcode encoding the identity of the drug therein, and the refill system 300 may be equipped to read the barcode once the cartridge is introduced. Alternatively, the cartridge may have an optical, RF, or similar ID tag or other electronic information storage (e.g., a ROM or an EPROM) that specifies the contents of the cartridge, and which is interrogated by the refill system 300.

Figure 5:
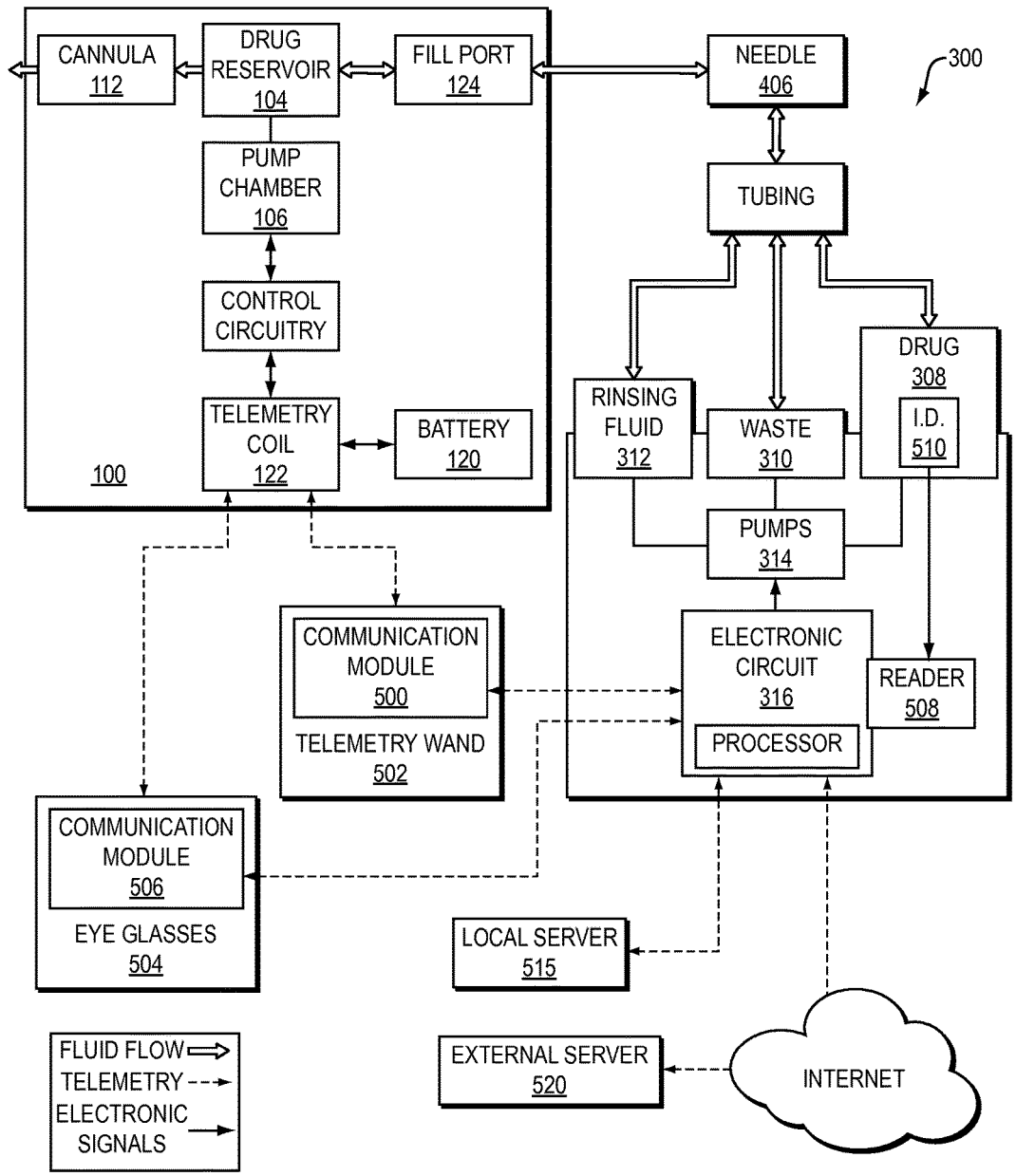
FIG. 5 is a block diagram of a drug pump device and refill system in accordance with various embodiments of the invention, illustrating communication links between various components of the system.

In various embodiments, the refill system 300 facilitates wireless communication with the drug pump device 100. For example, the control circuitry 316 of the base unit may include a radio-frequency (RF) transceiver or similar component that exchanges data with the induction coil 122 embedded in the pump device 100. In some embodiments, illustrated in block-diagram form in FIG. 5, a communication or telemetry module 500 (including a transceiver and related circuitry) is provided separately from the control circuitry 316, e.g., in a handheld telemetry wand 502 that allows the operator (e.g., a nurse or physician) to conveniently bring the wand in the vicinity of the implanted pump device 100, thereby reducing power requirements on the device 100 and, consequently, its footprint. The wand may be corded to the base unit, or communicate with the base unit via a separate wireless connection. In some embodiments, special eyeglasses 504 equipped with a telemetry module 506 are used to recharge the pump's battery 120 via the induction coil 122; such eyeglasses are described in U.S. Ser. No. 12/463,251, filed on May 8, 2009, the entire disclosure of which is hereby incorporated by reference. These eyeglasses 504 and the refill system 300 may be connected to each other or to a common console, and wireless data exchange with the drug pump device 100 may occur via the eyeglasses rather than a separate telemetry wand 502.

Via the telemetry module (of the telemetry wand 502 or the eyeglasses 504), the base unit may send refill information, including, e.g., the type of drug, the volume injected into the reservoir, a drug dosing schedule, and the date of refill, to the pump device 100. The drug pump device 100 may store this information in its on-board memory, preferably in encrypted form to ensure patient privacy, and may provide it when later interrogated by the refill system or other wireless device. The previous refill information may be used to ensure that the refill drug—as determined by the refill system's electronic label reader 508 from the barcode, RFID, optical ID, EPROM, or other electronic label 510 of the cartridge, or from the proprietary shape of the cartridge—matches the previously administered drug, thereby preventing off-label or other improper uses of the pump. Alternatively or additionally, the pump device 100 may be programmed to accept only a particular drug, and when wireless communication is established between the refill system 300 and the pump device 100, the refill system 300 and the pump exchange information to ensure that the refill drug matches the drug for which the pump was programmed. In either embodiment, refill is prevented—typically by disabling operation of the refill system—if a match is not registered. Of course, it may sometimes be necessary or desirable to change the drug administered to the patient, e.g., if a previously used drug caused complications. In this case, the operator may override the control signal that prevents the refill from commencing and/or reprogram the drug pump device 100 for the new drug.

The identity of the drug can also determine or limit the rate at which the pump dispenses the drug, or otherwise influence drug delivery by the implanted device 100. For example, in some embodiments, the drug pump device 100 is pre-programmed with different drug delivery protocols for two or more respective drugs (or, alternatively, with a generic drug delivery protocol including one or more variable parameters whose values depend on the type of drug to be administered). Based on the drug identified in the refill information, the drug pump device then selects one of the delivery protocols for execution. This functionality facilitates, e.g., easy testing of multiple alternative treatment agents for a particular disease, which may require different drug dosages, delivery intervals, etc., without necessitating re-programming of the drug pump device 100 when the treating physician decides to switch from one of the drugs to another.

The communication link established between the drug pump device 100 and the refill system 300 may also be used to download a stored drug dosing log or the pump operation history (including, e.g., information about any error conditions that have occurred in the pump device 100 since the previous communication) from the drug pump device 100. This information may be displayed on a screen (e.g., of a computer console that is part of the user interface 318) prior to commencement of the refill procedure, enabling the physician to detect any problems with the operation of the device 100 and relate the patient's condition to drug administration over extended periods of time. The physician may, for example, have the option to display twelve months of pump history or ten years of drug delivery history. Further, the physician may reprogram the drug pump device 100 at the time of refill, e.g., to adjust dosage protocols in response to changes in the patient's condition or new insights derived from medical research. In some embodiments, communication between the drug pump device 100 and the refill system 300 is sustained during the refill procedure to facilitate monitoring the process based on sensor readings acquired in the pump device 100. For example, sensors may continuously measure the pressure and fill stage of the drug reservoir 104, and send this data to the refill system 300, where it provides feedback to the processor of the control circuitry 316 and/or a physician manually controlling the refill system 300.

The data exchanged with the drug pump device 100 may be stored on a local server 515 integrated with or connected to the drug refill system 300. Alternatively, the communication module may permit the refill system 300 to communicate with an external server 520, e.g., remotely via the Internet. For example, the refill system 300 may have Wi-Fi, Zigbee, or a cellular phone chip (GSM, CDMA) that is constantly activated to cellular service or other wireless capability. This permits patient and drug data to be stored outside the refill system 300 ("in the cloud"), and may provide further levels of security and operational flexibility. Centralized information storage not only simplifies construction of the refill system 300 (e.g., by eliminating the need for a local server or for security systems required to comply with patient privacy regulations in case of local storage of patient data), but allows a particular patient's implanted pump to be interrogated and refilled by any refill system in any location, so long as communication with a remote central server can be established. Because the central server will have substantial storage capacity and, in various embodiments, the ability to autonomously query outside resources such as drug-interaction tables and manufacturer's information, levels of safety beyond drug matching may be implemented. Further, a central database may maintain (or link to) patient records and include database records associating the serial number of each implanted drug pump device 100 with the identity of the patient who received it. When the refill system 300 obtains the pump serial number through wireless communication with the pump device 100 and the identity of the drug in a newly inserted cartridge, it may communicate this information to the central server, which not only verifies the match but also reviews patient records to ensure that the drug and dosage remain appropriate for the patient (e.g., in light of additional drugs prescribed for the patient since the last pump refill).

Wireless communication between the pump and the refill system is preferably encrypted. The wireless circuitry is typically near-field and may utilize any suitable communication protocol, e.g., Bluetooth, Zigbee, or IrDa. Wireless communication between the refill system and the Internet, on the other hand, may take place via near-field or far-field wireless infrastructure. In some embodiments, the refill system establishes communication with the server via a wireless gateway serving the site where the system is used (and implementing, for example, the Wi-Fi protocol or another variant of the IEEE 802.11 standards). In other embodiments, a cellphone (e.g., GSM) chip is installed in the refill system 300, either as a primary communications platform or as a backup, should local wireless access prove unavailable. Of course, the refill system 300 may also communicate with the Internet through a wired connection (such as via Ethernet cables).

Figure 6:
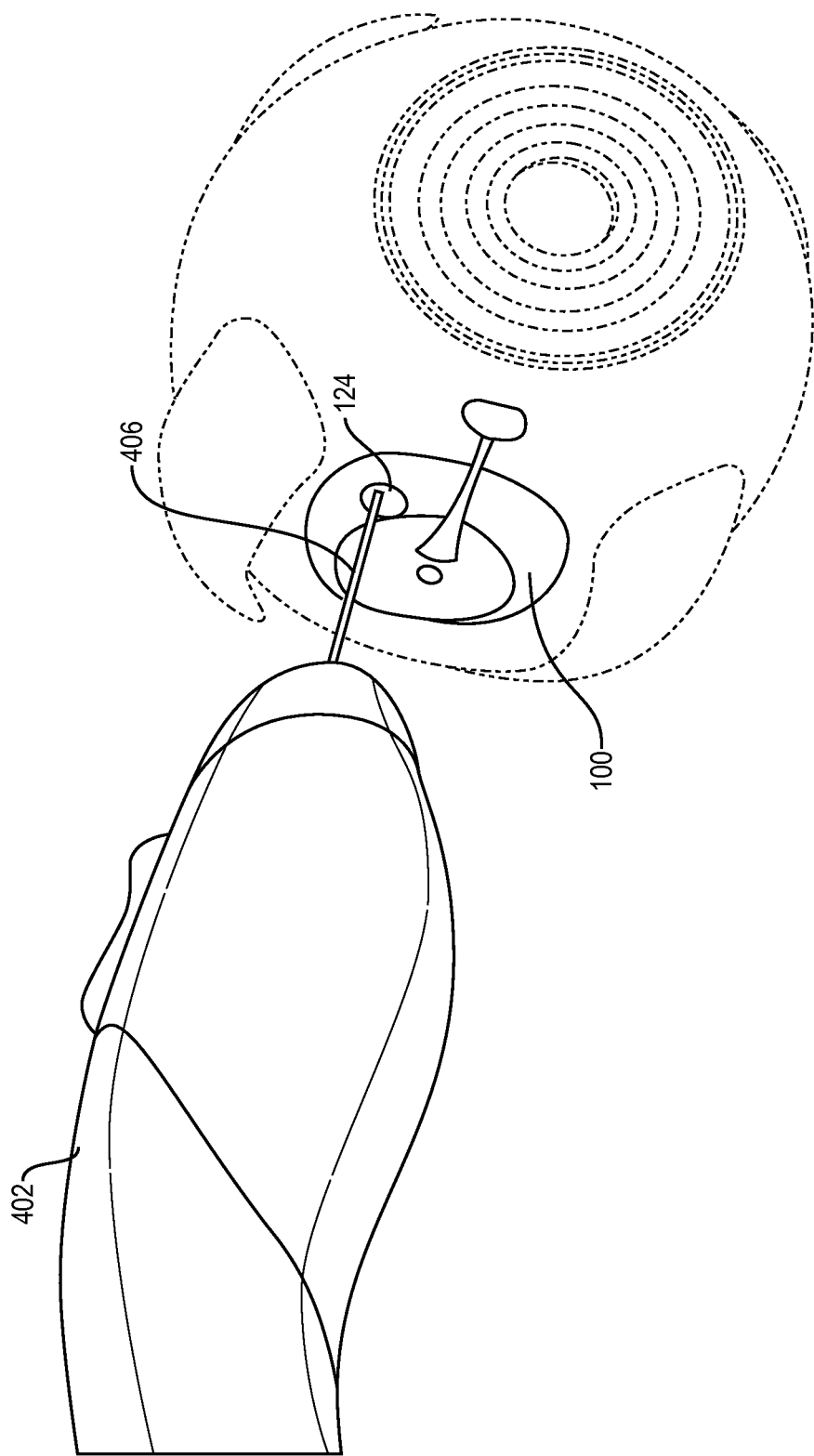
FIG. 6 is an isometric view illustrating insertion of a refill needle into the human eye in accordance with various embodiments of the invention.

The refill system 300 is typically prepared for use by introducing a drug-containing cartridge into the base unit or the hand-held refill tool 400 and establishing fluid communication between the cartridge and the outflow needle 406. The physician then manipulates the refill tool 400 to insert the needle into the drug reservoir 104 of the implanted device 100 via the fill port 124, as shown in FIG. 6. Various visual aids and sensing mechanisms may be integrated into the port 124 and/or the refill tool to aid the physician in locating the port 124 to protect the patient from inadvertent punctures by the needle, as well as to verify proper needle insertion before the refill pumps are activated.

In some embodiments, the needle entry port 124 is identified by means of a visualization ring surrounding the port aperture; various implementations of such a ring are described in U.S. patent application Ser. No. 12/348,178, the entire disclosure of which is hereby incorporated herein by reference. The visualization ring may include, for example, fluorescent pigments (e.g., excited by ultraviolet radiation), a light emitting diode, or a material that enhances surface echogenicity and acoustic shadowing. For example, if the refill port septum is made of silicone while the surrounding reservoir wall or refill port housing is made of a detectably different material, an ultrasonic probe may be incorporated into the refill tool to detect when the tool is located over the refill port septum. If the refill port housing is ultrasonically highly reflective, this probe can use the simple absence of ultrasonic reflection to detect the "hole" constituting the refill septum. Electronics may also be present in the drug-delivery device in order to move or vibrate the visualization ring so as to provide mechanical feedback to the physician regarding the location of the port 124. In other embodiments, the visualization ring includes a magnetic material or a coil generating a magnetic field that can be detected by a magnetic-field sensor integrated into the refill tool. Still other modalities to facilitate visualization of the refill port include optical coherence tomography and capacitive sensing. More than one modality may be employed for patients who form excessively fibrotic encapsulation around the implanted pump device 100, impeding visual identification.

The visualization ring (or the pump device itself) may be illuminated, in some embodiments, using a "transillumination" light source. In ophthalmic applications, the light source is typically held against the patient's eye. The light emitted by the light source may have a red, infrared (IR), or other wavelength (or wavelength band) optimized for penetrating the conjunctiva, or may be an excitation light for a photoluminescent material in the visualization ring and/or the pump. One approach is to use a stand-alone light source, e.g., a manipulable gooseneck lamp or one that the clinician may wear on his forehead. In another approach, the light source is integrated with the handheld refill tool that contains the refill needle, ensuring proper alignment between the light source and the needle, or combined with a tool to hold or grasp the pump device or other manipulator (leaving the surgeon's other hand free to fill the implant). For example, the procedure for refilling the pump may call for offsetting the conjunctiva over the refill port prior to needle insertion (to lower the chance of infection) and stabilizing the pump device and surrounding tissue during the needle insertion and refill process; a light can be combined or integrated with a suitable manipulator tool for offsetting the conjunctiva and stabilizing the eye. The light source can be a fiber-optic extension or an LED-based light source that has a bendable neck so that the tip of the flexible tube (with the light source at the end) can be placed optimally. Depending on the placement of the pump device and the variability of the surgeon's desired approach, a movable light source with a bendable neck may be desirable in order to target the light in a safe location.

Once the proper entry site has been identified and the needle has punctured the refill plug or septum, it is important to ensure, prior to injecting medication, that the refill needle fully penetrates the septum and is located at the reservoir-side of the refill port. Otherwise, if the practitioner does not fully insert the needle into the pump refill port but instead stops short and injects the medication into body tissue, so-called "pocket fills" can occur. Injecting highly concentrated medicine into the body instead of the pump device can be hazardous or even fatal.

One approach to ensuring proper needle insertion, which is applicable, e.g., to ophthalmic drug pump devices, is to use IR illumination that penetrates the conjunctiva and an IR camera (placed outside the eye) imaging through the conjunctiva to visualize the needle as it is guided. IR radiation enables imaging the interior of the fill port 124, provided the port housing or walls are not made of metal. Illumination may be achieved with the same types of light sources as described above in the context of visualizing the refill port 124 to find the correct puncture site, including, e.g., a light source integrated into the refill tool. The IR camera images may be displayed on an IR monitor (or, optionally after image processing, on a general-purpose screen of the user interface of the refill system), or in a goggle worn by the physician or a retinal display.

Figure 7A:
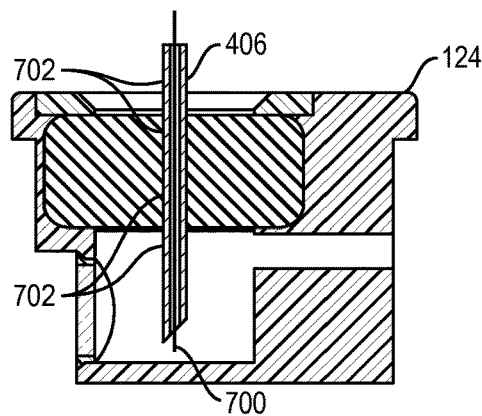
FIGS. 7A-7G are side views of refill ports with integrated mechanism for sensing needle insertion in accordance with various embodiments of the invention.

Visual confirmation that the refill needle has been inserted by the desired amount (or "bottomed out") may also be provided, as shown in FIG. 7A, by a wire 700 integrated inside the refill needle 406, which protrudes a certain amount from the refill tool 400 when the needle is in the proper position. Alternatively or additionally, a series of marks 702 on the refill needle may be used to gauge how far the needle 406 has been inserted. The needle may also have a mechanical stop of a diameter exceeding that of the aperture of the refill port, and positioned such that the needle is correctly positioned within the reservoir when the stop reaches the port or an overlying tissue layer (e.g., in ophthalmic applications, the conjunctiva); exemplary stops are described, e.g., in U.S. patent application Ser. No. 12/348,178.

In another approach, one or more sensors integrated into the refill port 124 and/or the refill tool 400 are used to confirm proper needle position within the refill port. For example, a line-of-sight optical sensor may be employed. The sensor pair includes an optical emitter (e.g., an LED) and detector (e.g., a photodiode) placed on opposite sides of the refill port 124—e.g., in simple port embodiments as shown in FIG. 2A, on opposite sides of the wall defining the port aperture, or, in port embodiments including a port chamber separate from the drug reservoir as shown in FIG. 2E, on opposite sides of the chamber wall—so as to establish a light path across the port 124; light send by the emitter and received by the detector results in an electronic signal in associated sensor circuitry. When the needle is inserted into the refill port 124, the light path is blocked and the signal, consequently, interrupted, enabling the sensor to detect the needle. Similarly, an acoustic wave emitter and detector (operating, e.g., in the ultrasound regime or within another frequency range) may be disposed on opposite sides of the refill port. When the needle is inserted, the acoustic impedance (as indicated by the strength of the signal from the acoustic detector) will change, facilitating needle detection.

Figure 7B:
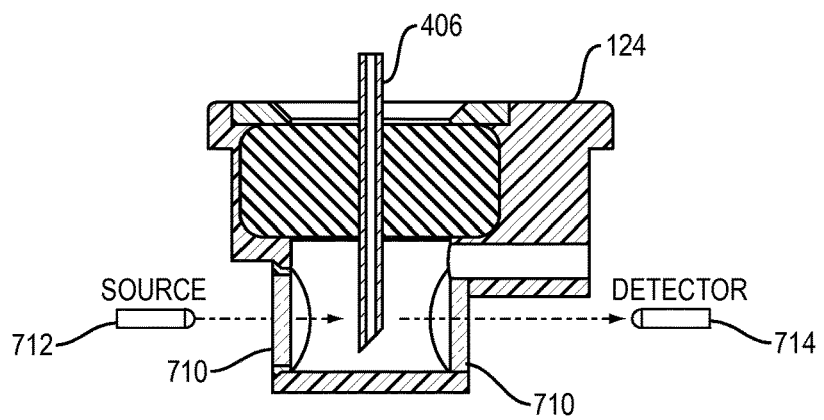

In some embodiments, illustrated in FIG. 7B, the optical detector-emitter pair is not located inside the refill port 124, but instead outside opposing optical windows 710 in the side wall of the port chamber. The windows 710 are positioned such that, when the needle is properly inserted, the optical signal path between the emitter 712 and the detector 714 is interrupted at least partially, which may be detected with suitable circuitry (as explained above). In an alternative embodiment, one of the windows 710 is replaced with an optical reflector placed at the interior port chamber wall, and the detector is located next to the emitter outside a single window. In this case, the inserted needle 406 blocks the light path between the emitter and reflector (and, similarly, between the reflector and detector) at least partially, reducing the reflected light measured by the detector.

Figure 7C:
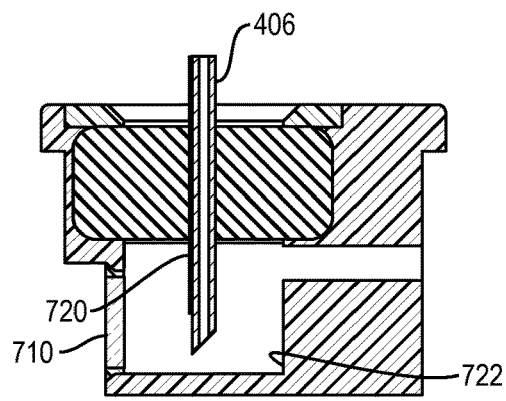

In yet another embodiment, illustrated in FIG. 7C, visualization and/or optical detection of needle insertion are achieved by integrating an optical fiber 720 with the needle that terminates at the needle tip (or, generally, a portion of the needle that is placed inside the fill port when the needle bottoms out) so as to illuminate the interior walls of the fill port once the needle 406 has been inserted. The optical fiber 720 may be attached to the exterior wall of the needle 406 and, optionally, be clad with a protective coating, or it may be provided inside the needle 406, e.g., in the second lumen of a dual-lumen needle with a side opening for light emission. The optical signal indicative of proper needle insertion may be captured with a suitable sensor in the port, or observed by eye, e.g., through an optical window 710 in the port wall. The sensor may also be placed on the optical window 710. To avoid light penetrating through the septum before needle insertion, the septum material is generally optically opaque. The interior walls of the fill port 722 may be highly reflective so as to reflect at least a portion of the light from the optical fiber to the sensor or the optical window 710.

Figure 7D:
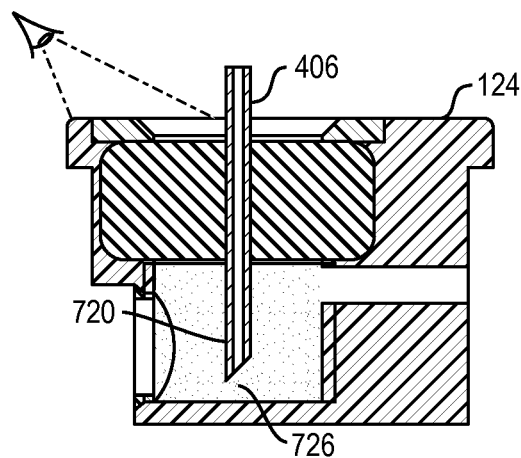

In a modified embodiment, illustrated in FIG. 7D, a luminescent (e.g., fluorescent) material 726 is used in the needle port 124 and/or the drug reservoir 104 (e.g., applied as a coating to portions of the walls of the port or reservoir) in conjunction with a light source provided at the needle tip that emits light at wavelengths inducing luminescence. For example, an optical fiber 720 integrated into the needle may be connected to a light source external to the needle and provide light via an exit face at the needle tip (or, generally, at a portion of the needle that will be located inside the reservoir or port when the needle is properly positioned for refill) so as to irradiate the luminescent material 726 once the needle 406 has been inserted. The luminescent signal indicative of proper needle insertion may be captured with a suitable sensor in the port 124 or reservoir 104, or observed by eye, e.g., through an optical window in the port or reservoir wall. To filter out the original emission and ambient light, the detector or optical window may be equipped with a suitable optical filter or dichroic mirror. Alternatively, all of the light may be captured by a CCD camera (e.g., placed outside the optical window), and the luminescent signal may be separated from the background via frequency-filter algorithms applied during image processing.

In some embodiments, the fluorescent light can also be observed through the septum if, for example, the septum is transparent. If fluorescent materials are also used to guide needle insertion (e.g., via a visualization ring), care must be taken in the design so that light emitted by the light source prior to insertion but passing through the septum does not excite the fluorescent material in the reservoir even when the needle is still outside the port.

Figure 7E:
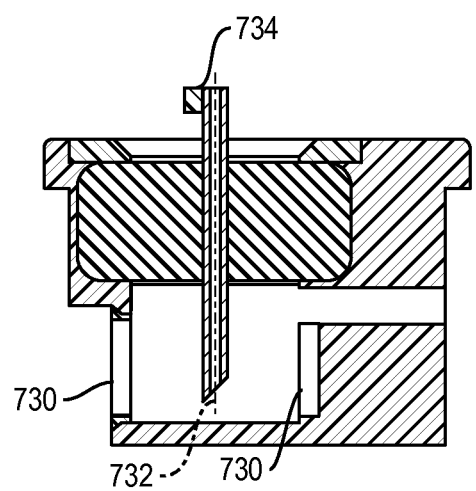

In alternative embodiments, electrical or magnetic sensors are employed. For example, two electrodes can be disposed on opposite sides of the refill port to measure electrical impedance (or capacitance) between them. If a needle is inserted, the impedance changes and varies with needle position until the needle is fully inserted. Similarly, magnetic or inductive position sensors that utilize one or more induction coils in the refill port in conjunction with a ferromagnetic needle (or a needle incorporating ferromagnetic material along a portion of its length) may be used. The coil(s) inside the refill port may sense the presence and, in some implementations, the position of the needle within the port. In one embodiment, the sensor operates in a manner analogous to a linear variable differential transformer (a common type of electromechanical transducer that converts rectilinear motion into a corresponding electrical signal). For example, three solenoids may be placed end-to-end around the port aperture. An alternating current drives the center coil, inducing a voltage in the top and bottom coils when the ferromagnetic portion of the needle provides a common core linking the solenoids. As the needle moves, the center coil's linkage to the two neighboring coils changes and causes the induced voltages to change. In other magnetic-sensor embodiments, as shown in FIG. 7E, coils or permanent magnets 730 are used to create a magnetic field in the port, preferably with a locally maximum field strength along a (substantially central) axis 732 through the port (i.e., along the desired needle insertion path). The magnets may, for example, be integrated into the wall of the port, or the entire wall may be made of, or coated with, a magnetic material. A magnetic-field sensor 734 integrated with the needle is employed to detect the region of highest field strength, providing feedback for the guidance of the needle along the axis through the port. Ideally, the magnetic-field sensor 734 is provided at the needle tip, but even if the sensor is not located between the magnets 730, it may be able to measure portions of the magnetic field generated thereby. Conversely, the field-generating coil (or permanent magnet) may be integrated into the needle (or the needle be made of or coated with a magnetic material), and the magnetic-field sensors provided in the refill port.

Figure 7F:
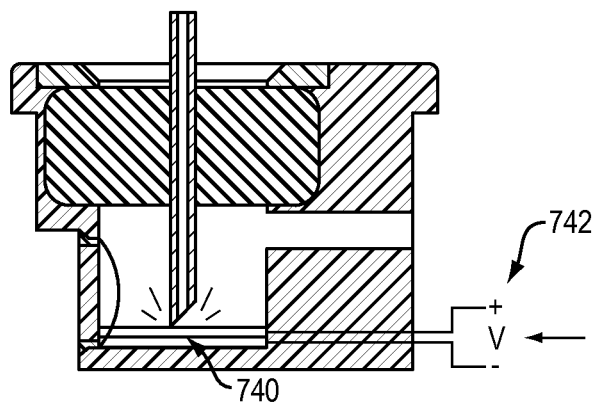
Figure 7G:
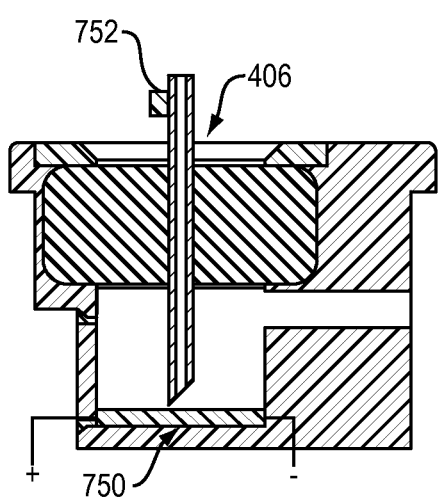

Another way to ensure that the refill needle has fully entered the pump device 100 through the refill port 124 is to use a mechanical switch at the bottom of the refill port 124 that activates when the needle strikes it. The switch may, for example, be disposed on the bottom of a port chamber (opposite the aperture) such as the one shown in FIG. 7F, or mounted on a needle stop 220 as shown in FIG. 2C. In yet another embodiment, the needle is permitted to penetrate the entire interior of the drug reservoir 104 and stopped at the reservoir wall opposite the refill port 124, in which case the switch may be disposed on this opposite wall. Instead of a mechanical switch, a piezo-electric element 740 with associated circuitry may be used. When the (fully inserted) needle 406 exerts force against the piezo-element 740, a voltage 742 is induced across the element, and this voltage can be measured by the associated circuitry. Another approach, illustrated in FIG. 7G, involves including the needle itself as part of an electrical circuit, e.g., by applying a small voltage to a conductive plate 750 (e.g., of metal or a resistive material such as a conductive polymer) at the bottom of the refill port and using the needle to detect this voltage with a suitable sensor 752 upon contacting the plate 750. If the needle 406, when in contact with the conductive bottom plate 750, along with the detection circuitry presents an impedance less than or not excessively greater than that of the electrical path through the bottom plate 750, a detectable electrical current can be diverted through the needle 406. The impedance difference is not excessive so long as the measurement circuitry can reliably detect the current. For example, in various embodiments, the impedance ratio of the detection circuitry to the electrical path through the bottom plate 750 is no more than 10, no more than 100, or no more than 1000, depending on the sensitivity and characteristics of the detection circuitry.

In the various sensor embodiments described above, complete insertion of the needle generally causes creation of an electrical signal in the circuitry associated with the sensor, which may be embedded in the drug pump device 100 and/or the refill tool. Signals generated in the pump device 100 may be communicated to the refill system 300 via the wireless link between the pump device 100 and the telemetry wand (or eyeglasses), whereas signals measured in the refill tool may be send to the base unit of the refill system 300, e.g., via a data cable. The control circuitry 316 of the base unit may condition activation of the refill pumps on receipt of a signal indicative of proper needle insertion.

Still another way of ensuring complete entry of the needle relies on the activation of the (e.g., electrolysis) pump of the implanted drug pump device 100 to provide detectable sub-dosing pressure (e.g., pressure lower than that used during drug delivery to the patient's body) on the residual drug in the drug reservoir 104. The refill system 300 detects this fluid as it is forced into the refill needle when the needle is in the proper location within the port. For example, the refill system may directly detect fluid pressure in the needle or fluid flow into the refill device via a suitable pressure or flow sensor, or the practitioner can visually observe fluid traveling into the needle and/or attached tubing. Placement of the needle in the port may thus be confirmed prior to proceeding with the refilling procedure. Of course, this approach depends on avoiding full depletion of drug from the pump reservoir. An alternative is to inject saline solution (which would not harm the patient if accidentally injected into tissue) into the drug reservoir 104 and then activate the pump to determine whether the fluid is forced back into the refill system. Here, too, the pump must be able to maintain or produce sub-pumping pressure on the drug reservoir. Alternatively, the pump can be configured to operate at a very low dosing amount and rate, such that pressure is developed, but little if any drug (or other fluid) is dosed while the needle location is confirmed. Yet another embodiment exploits the fact that the drug reservoir 104 is, in the natural rest state of the drug pump device 100, under a slight vacuum. Therefore, if a pressure sensor in the needle 406 detects a vacuum pressure, this is indicative of fluid communication between the needle and drug reservoir.

Following proper introduction of the needle into the refill port or reservoir, the refill pumps are activated to withdraw any remaining drug fluid from the reservoir, inject and aspirate rinsing fluid (typically in multiple cycles), and finally refill the reservoir 104 with new drug. This entire process is preferably carefully monitored by the control circuitry and/or the treating physician to facilitate proper adjustments of pump pressures and flow rates, valve settings, etc. and detect any problems. For this purpose, the refill system 300 (including the refill tool) and/or the drug pump device 100 may be equipped with flow, pressure, and other sensors. For example, during the fill process, the pressure inside the drug reservoir 104 alternates between a negative value (while material is vacuumed out) and a positive value (while drug is being introduced). One or more pressure sensors integrated in the drug reservoir and/or the refill port can be employed to monitor this process and ensure proper operation as well as reservoir integrity. For example, if certain expected pressure levels are not reached, this may indicate a leak in the reservoir or elsewhere. Sensor feedback may immediately be provided to the refill system 300 via the wireless telemetry link. Pressure sensors may also be placed into the refill pumps 314. If the pressure detected in the reservoir 104 matches that applied by the pump of the refill system 300, successful refill is ensured. Flow sensors may be integrated, for example, into the refill needle, the channels connecting the needle to the cartridges, and the refill port, and may serve to keep injection rates within safe limits. Furthermore, a vision-based (e.g., camera) system may be employed to track the drug pump device 100 and the site where it is implanted (e.g., the patient's eye) during refill. The drug reservoir 104 may also include chemical sensors for monitoring drug potency, and/or viscosity sensors that detect if the drug denatures and changes in structure. The various sensors may also serve to monitor reservoir integrity outside the refill process. Problems can be inferred, for example, from any sudden change in pressure, viscosity, or chemical characteristics.

In various embodiments, the drug reservoir 104 of the pump is formed from a collapsible membrane and is covered with a hard outer shell 116, which protects the reservoir 104 from accidental compression by body tissues or outside forces. The drug is forced out of the reservoir 104 under pressure from a separate electrolysis chamber 106, which is expanded via hydrolysis. After each active dosing cycle, hydrolysis ends and the electrolyte returns to a liquid state. The contents of drug reservoir 104 are reduced by the amount of drug dosed during that cycle, and so the combined volume of the drug reservoir 104 and deflated electrolyte chamber 106 is smaller after each dosing cycle. If the drug reservoir and electrolyte chamber were contained within a fixed-volume shell 116, a vacuum would develop which would then need to be overcome with additional hydrolysis each cycle.

A large hole in the hard shell is one solution to allowing fluid to flow in under the hard shell to balance the negative pressure created by the diminishing drug reservoir. Upon completion of the drug-dosing cycle, bodily fluid is drawn in through the hole to replace the drug ejected from the reservoir. With a sufficiently large hole, upon the next cycle of dosing this bodily fluid is forced back out, and thus the electrolyte chamber must be inflated past the previous volume in order to dose new drug from the reservoir. This design is progressively inefficient, as the expansion required of the electrolyte chamber increases with decreasing volume of drug remaining in the drug reservoir.

If the pump is implanted such that the drug reservoir is full for a long enough time that tissue encapsulation around the implant fully develops, and is stable, then the encapsulation overlying the hole in the hard shell may act as a biological valve, allowing out-flow of fluid but serving as a "leaky" check-valve that prevents the free flow of fluid back into the space under the hard shell. Fluid can be expected to pass slowly under these circumstances, balancing the depleted volume of the drug reservoir.

Assuming the hole is sized to prevent growth of tissue in and under the hard shell, difficulties may be encountered during evacuation, flushing and refill of the drug reservoir. In these circumstances, pressure-balancing fluid from the body will only slowly enter under the hard shell (due to the valve effect of the overlying tissue), greatly increasing the amount of time a drug removal/flush/refill cycle can take. In this case, it is desirable to balance pressure when attempting to remove fluid from the drug reservoir.

One way to provide a volumetric offset to allow removal of fluid from the drug reservoir relies on the pump's electrolyte readily vaporizing under negative pressure. If the electrolyte gasses under mild negative pressure, and the hard shell is sufficiently strong to withstand negative pressure, then suction placed on the refill port will easily remove fluid from the drug reservoir, as the electrolyte chamber inflates under the resulting negative pressure. The tube for conducting fluid between the drug reservoir and the refill port will be sufficiently strong to withstand negative pressure without collapse.

In this case, inflating and deflating the drug reservoir during removal of unused drug, the inflow of flushing fluid, removal of flushing fluid and the final inflow of new medication is balanced by the phase conversion of the electrolyte to and from the gaseous state. If the electrolyte is chosen appropriately, this process occurs quickly and with only minimal negative pressure exerted on the system. If the free flow of fluid out from under the hard shell must be restricted, however (e.g., by the use of very small holes or a semi-permeable membrane), then the foregoing approach may not allow enough time for the fluid to be forced out prior to refill. In particular, removal of body fluid through the small holes or membrane in the hard shell may take too long to be performed during the refill procedure with a needle residing in the refill port.

In this case, the pump may be activated in a "re-establish volume" mode whereby the dosing rate is set extremely low, or else the pump may be operated in a sub-pumping pressure mode such that the bodily fluid is forced out through the hard shell over an extended period of time, prior to refill. Using the pump electrolyte to balance pressures during the refill procedure presumes an electrolyte chamber that can fully inflate to nearly the entire volume under the hard shell. One way to balance negative pressure resulting from removal of fluid from the drug reservoir is to activate the pump in a very low dosing mode or sub-pumping pressure mode such that the electrolyte chamber is inflated as drug exits the drug reservoir. In effect, the inflating electrolyte chamber is used to balance negative pressure created by withdrawal of fluid from the drug reservoir. Fluid injected into the drug reservoir pressurizes the electrolyte chamber, forcing the electrolyte back into a liquid state. The electrolyte is chosen to return to a liquid state in a reasonable amount of time in order to minimize the time necessary for the refill procedure.

Alternatively, the pump itself may actively force fluid out of the drug reservoir by inflating the electrolyte chamber to pressurize the drug reservoir, forcing drug from the reservoir through a needle inserted into the refill chamber, with the refill device remaining passive during withdrawal of fluid. A needle is inserted prior to inflating the electrolyte chamber, or the pump is operated in a sub-pumping pressure mode (where the pressure developed on the electrolyte and drug reservoirs is below that of the cannula check valve to prevent dosing).

If a port is provided directly to the outer chamber where bodily fluid accumulates under the hard shell, then withdrawal of unused drug from the reservoir, flushing and replenishment with new drug can be achieved quickly and easily therethrough—i.e., this port permits the free flow of pressure-balancing fluid throughout the procedure, facilitating its rapid completion. But in order to retain the added efficiency that results from restricting the movement of the fluid in the outer chamber, a reliable septum should also be included in this port in order to prevent fluid from escaping the outer chamber during drug dosing. If such a fluid-flow restriction is not desired or needed, the additional port can be structurally simple, and the septum need only prevent tissue from growing in and obstructing access.

An additional port to allow fluid flow in and out of the outer chamber under the hard shell requires its own needle. Any of a variety of configurations can accommodate this requirement. In one implementation, the outer chamber has an entirely separate access port area into which a small butterfly needle is inserted. This needle may contain a small amount of saline in a collapsible reservoir, allowing it to remain passively in place throughout the procedure, with fluid flowing in and out of the needle reservoir while the refill system operates. The sequence is as follows: (1) when the refill system withdraws remaining unused drug from drug reservoir, saline flows into the outer chamber from the second needle to match the aspirated volume; (2) when flushing fluid is injected into the drug reservoir, saline flows out of the outer chamber into the second needle reservoir, (3) when the flushing fluid is withdrawn from the drug reservoir, saline flows back into the outer chamber, and (4) when new drug is injected into drug reservoir, saline flows back into the second needle reservoir. After completion of this process, both needles are removed.

Figure 8A:
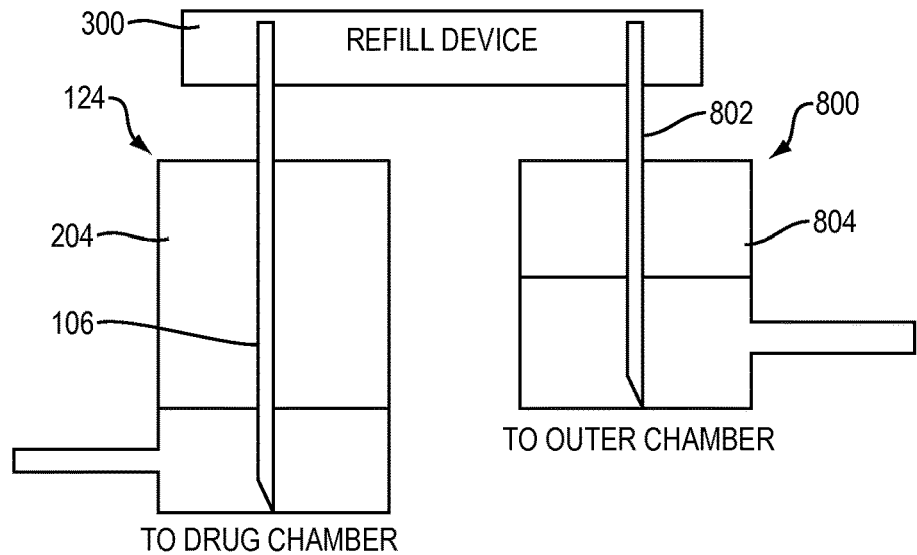
FIGS. 8A and 8B are side views of two side-by-side ports and a dual-septum port, respectively, for facilitating refill of the drug reservoir and simultaneous pressure balancing through access to an outer chamber of the drug pump device, in accordance with various embodiments of the invention.

The two needles, along with the waste/saline reservoir for the outer chamber, may also be incorporated into one refill device. For example, as illustrated in FIG. 8A, the two ports 124, 800 may be placed side-by-side such that both needles 106, 802 enter the pump device 100 simultaneously. The two needles 106, 802 may, for example, have different lengths and the two port septums 204, 804 may have different thicknesses to prevent the needles from fully entering the wrong port. Active pump pressure sensing may also assist in detecting if the needles are correctly placed in the ports.

Figure 8B:
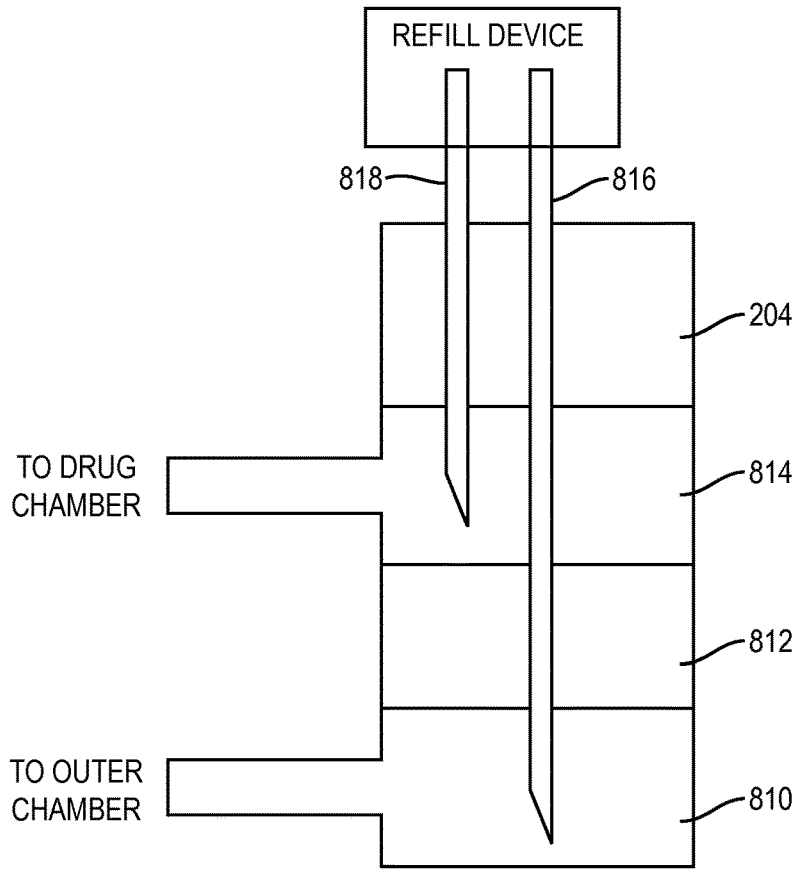

Alternatively, a single, dual-septum port may be employed, as shown in FIG. 8B. For example, a communicating space 810 below the first septum 812 may lead to the outer chamber, with the communicating space 814 underneath the second septum 204 leading to the drug reservoir 104. The refill device has two needles, one longer than the other, such that when the longer needle 816 is fully inserted into the dual-septum port (i.e., into the lower communicating port), the shorter needle 818 resides in the upper port. The two needles cannot being mistakenly interchanged, because the lower port would always communicate with one chamber of the implant while the upper port could only communicate with the other. When properly inserted, the two needles push and/or pull the unused drug, flushing fluid and replenishing drug as appropriate.

Having described certain embodiments of the invention, it will be apparent to those of ordinary skill in the art that other embodiments incorporating the concepts disclosed herein may be used without departing from the spirit and scope of the invention. For example, various features described with respect to one particular device type and configuration may be implemented in other types of devices and alternative device configurations as well. Accordingly, the described embodiments are to be considered in all respects as only illustrative and not restrictive.

What is claimed is:

1. A combination comprising an implanted, refillable drug pump device and an external system for filling the implanted, refillable drug pump device, the combination comprising:
   an implanted, refillable drug pump device comprising a memory and a drug reservoir with a fill port;
   a needle for insertion into the fill port of the implanted drug pump device; and
   an external refill system for refilling the implanted pump device via the needle, the refill system comprising:
      at least one fluid container fluidly connectable to the needle and to the drug reservoir therethrough;
      at least one pump for causing fluid flow through the needle between the at least one fluid container and the drug reservoir;
      electronic circuitry including a processor for controlling operation of the at least one pump to perform a refill operation; and
      a wireless communication module facilitating wireless data exchange between the electronic circuitry of the external refill system and the implanted drug pump device for wirelessly obtaining sensor data from sensors in the implanted drug pump and transmitting the obtained sensor data to the electronic circuitry, wherein the electronic circuitry is configured to (i) determine refill information based on the sensor data and (ii) cause the wireless communication module to send the determined refill information to the implanted, refillable drug pump device for storage in the memory thereof,
   wherein the refill information comprises at least one of a volume injected into the reservoir, a type of drug, a drug dosing schedule, or a date of refill, and the electronic circuitry is configured to perform the refill operation by controlling the at least one pump based at least in part on the obtained sensor data, the refill information sent from the wireless communication module and stored in the memory, and a current fill level of the drug reservoir.

2. The combination of claim 1, further comprising: tubing for fluidically connecting the at least one fluid container to the needle.

3. The combination of claim 1, wherein the wireless communication module is integrated in the electronic circuitry.

4. The combination of claim 1, wherein the wireless communication module is integrated in a handheld telemetry wand in communication with the electronic circuitry.

5. The combination of claim 1, wherein the wireless communication module is integrated in patient-worn eyeglasses in communication with the electronic circuitry.

6. The combination of claim 1, wherein the sensor data comprises sensor readings of sensors disposed in the drug reservoir.

7. The combination of claim 1, wherein the wireless data comprises information indicative of a type of drug to be administered.

8. The combination of claim 1, wherein the wireless data comprises information indicative of an error condition that has occurred in the drug pump device since a previous communication between the electronic circuitry and the drug pump device.

9. The combination of claim 1, wherein the electronic circuitry is configured to control pump operation based, at least in part, on sensor readings of at least one of flow sensors or pressure sensors disposed in at least one of the needle, the at least one pump, or a fluidic connection between the needle and the at least one fluid container.

10. The combination of claim 1, wherein the wireless communication module is configured to retrieve refill information previously sent from the external refill system and stored in the implanted drug pump device, the electronic circuitry being configured to perform the refill operation by controlling the at least one pump based at least in part on the retrieved refill information.

11. The combination of claim 9, wherein the refill information comprises at least one of a type of drug, an amount of drug, a dosing schedule, or a refill date.

12. The combination of claim 1, wherein the at least one fluid container comprises a drug-containing cartridge.

13. The combination of claim 12, wherein the at least one fluid container further comprises at least one of a waste-fluid receptacle or a rinsing-fluid-containing cartridge.

14. The combination of claim 12, wherein the drug-containing cartridge comprises a label indicative of a type of drug contained in the cartridge.

15. The combination of claim 14, wherein the label comprises at least one of a barcode, an RFID, an optical ID, or an EPROM.

16. The combination of claim 14, further comprising a reader for reading the label.

17. The combination of claim 14, wherein the electronic circuitry activates the at least one pump so as to cause fluid flow from the drug-containing cartridge to the drug reservoir only if the type of drug indicated by the label matches a type of drug to be administered as determined based on data received from the implanted drug pump device via the wireless communication module.

18. The combination of claim 12, wherein the drug-containing cartridge has a shape indicative of a type of drug contained in the cartridge.

19. The combination of claim 1, wherein the electronic circuitry further facilitates data exchange with an external server.

20. The combination of claim 19, wherein the data exchanged with the external server comprises a serial number of the implanted drug pump device and data associated therewith, the serial number being received by the system from the implanted drug pump device via the wireless communication module.

21. The combination of claim 20, wherein the data associated with the serial number of the implanted drug pump device comprises at least one of patient data, a drug dosage log, or a drug pump device history.

22. A combination comprising an implanted, refillable drug pump device and a system for filling the implanted, refillable drug pump device, the combination comprising:
    an implanted, refillable drug pump device comprising a memory and a drug reservoir with a fill port;
    a base unit comprising (i) a pump for causing fluid flow through a fluidic connection between a drug-containing cartridge and the drug reservoir, and (ii) electronic circuitry including a processor for controlling operation of the pump; and
    in communication with the base unit, a wireless communication module facilitating wireless data exchange with the implanted, refillable drug pump device and configured to send drug delivery protocols for storage in the memory of the implanted, refillable drug pump, the data including an identification of the drug in the cartridge, wherein the electronic circuitry of the base unit is configured to provide new programming to the implanted drug pump device based on the identification, if the identification does not match a drug that the implanted, refillable drug pump device was previously programmed to accept, the new programming causing the implanted, refillable drug pump device to accept the drug in the cartridge, retrieve a new drug delivery protocol associated with the identification from the drug delivery protocols sent from the wireless communication module and stored in the memory, and execute the retrieved drug delivery protocol.

23. A method of verifying proper selection of a drug prior to injection thereof by a refill system into a drug reservoir of an implanted drug pump device, the method comprising the steps of:
    receiving a drug cartridge in a well of the refill system, the drug cartridge having an electronically readable label indicative of a drug contained in the cartridge;
    causing the refill system to electronically read the label,
    causing the refill system to (i) receive, from the implanted drug pump device via a wireless communication module of the refill system, data indicative of a drug to be administered and (ii) send drug delivery protocols to the implanted drug pump device, via the wireless communication module, for storage in a memory associated with the implanted drug pump device, the data including an identification of the drug in the cartridge; and
    causing the refill system to determine whether the drug indicated by the label matches the drug to be administered, and
    in accordance with a determination that the drug indicated by the label does not match the drug to be administered, upon operator command providing new programming to the implanted drug pump device to cause the implanted drug device to accept the drug in the cartridge, retrieve a new drug delivery protocol associated with the drug from the drug delivery protocols sent from the wireless communication module and stored in the memory, and execute the retrieved drug delivery protocol, and
    in accordance with a determination that the drug indicated by the label matches the drug to be administered, injecting the drug into the reservoir.

24. The combination of claim 22, wherein the wireless communication module is configured to send the new drug-delivery protocol to the implanted drug pump device for storage therein.

25. The combination of claim 23, wherein the wireless communication module is configured to send the new drug-delivery protocol to the implanted drug pump device for storage therein.

26. The combination of claim 1, wherein the drug reservoir is collapsible.

27. The combination of claim 1, wherein the refill information further comprises at least one of a drug dosing log or an operating history comprising information about an error condition that has occurred in the implanted, refillable drug pump device.

* * * * *